(12) United States Patent
Mai et al.

(10) Patent No.: US 7,801,682 B2
(45) Date of Patent: Sep. 21, 2010

(54) METHOD OF MONITORING GENOMIC INSTABILITY USING 3D MICROSCOPY AND ANALYSIS

(75) Inventors: Sabine Mai, Winnipeg (CA); Tony Chih Yuan Chuang, Baltimore, MD (US); Sharareh Moshir, Vienna (AT); Yuval Garini, D.N. Misgav (IL)

(73) Assignee: Cancercare Manitoba, Winnipeg, Manitoba (CA)

( * ) Notice: Subject to any disclaimer, the term of this patent is extended or adjusted under 35 U.S.C. 154(b) by 948 days.

(21) Appl. No.: 10/546,152

(22) PCT Filed: Feb. 23, 2004

(86) PCT No.: PCT/CA2004/000241

§ 371 (c)(1),
(2), (4) Date: Aug. 22, 2005

(87) PCT Pub. No.: WO2004/074500

PCT Pub. Date: Sep. 2, 2004

(65) Prior Publication Data

US 2007/0031831 A1    Feb. 8, 2007

Related U.S. Application Data

(60) Provisional application No. 60/448,545, filed on Feb. 21, 2003.

(51) Int. Cl.
*G06F 19/00* (2006.01)
*G06K 9/20* (2006.01)
*G06K 9/36* (2006.01)
*G06K 9/00* (2006.01)

(52) U.S. Cl. .......................... 702/19; 382/133; 382/282; 382/286

(58) Field of Classification Search ........................ None
See application file for complete search history.

(56) References Cited

U.S. PATENT DOCUMENTS 6,506,563 B1    1/2003    Ward et al.

OTHER PUBLICATIONS

Maierhofer Christine, et al., Multicolor Deconvolution Microscopy of Thick Biological Specimens, American Journal of Pathology, Feb. 2003.
Schaefer L.H., et al., Geberalized Approach for Accelerated Maximum Likelihood Based Image Restoration Applied to Three-dimensional Fluorescence Microscopy, Journal of Microscopy, Nov. 2001.
Henderson S., et al., In Situ Analysis of Changes in Telomere Size During Replicative Aging and Cell Transformation, The Journal of Cell Biology, Jul. 1996.
Bass Hank W., et al., Telomeres Cluster de Novo Before The Initiation of Synapsis: A Three-dimensional Spatial Analysis of Telomere Posistions Before and During Meiotic Prophase, Journal of Cell Biology, 1997, pp. 5-18, vol. 137.
Weirich Claudia, et al., Three-dimensional arrangements of Centromeres and Telomeres in Nuclei of Human and Murine Lymphocytes, Chromosome Research, 2003, pp. 485-502, vol. 11.
Chuang Tony Chin Yuan et al., The Three-dimensional Organization of Telomeres in the Nucleus of Mammalian Cells, Retrieved from the Internet,URL: http://www.biomedcentral.com/1741-7007/2/12, Jun. 2004.
Raz, Vered, et al., "Changes in lamina structure are followed by spatial reorganization of heterochromatic regions in caspase-8-activated human mesenchymal stem cells", Journal of Cell Science 119(20), Sep. 26, 2006, pp. 4247-4256.
Gonzalez-Suarez, Ignacio, et al., "Novel roles for A-type lamins in telomere biology and the DNA damage response pathway", The EMBO Journal (2009) 28, pp. 2414-2427.

*Primary Examiner*—Lori A Clow
(74) *Attorney, Agent, or Firm*—Kramer & Amado, P.C.

(57) ABSTRACT

The present invention relates to a method of detecting and monitoring genomic instability in a cell using three-dimensional analysis to assess telomeric and/or chromosomal organization. In addition, the invention relates to a method and system for characterizing the 3D organization of telomeres and/or chromosomes. The system includes an input module for inputting image data of the 3D organization of telomeres and/or chromosomes and a characteristic module for finding a parameter of the 3D organization. The invention also relates to the use of the three-dimensional analysis to detect, diagnose or monitor disease, particularly proliferative diseases such as cancer.

54 Claims, 19 Drawing Sheets

Figure 1
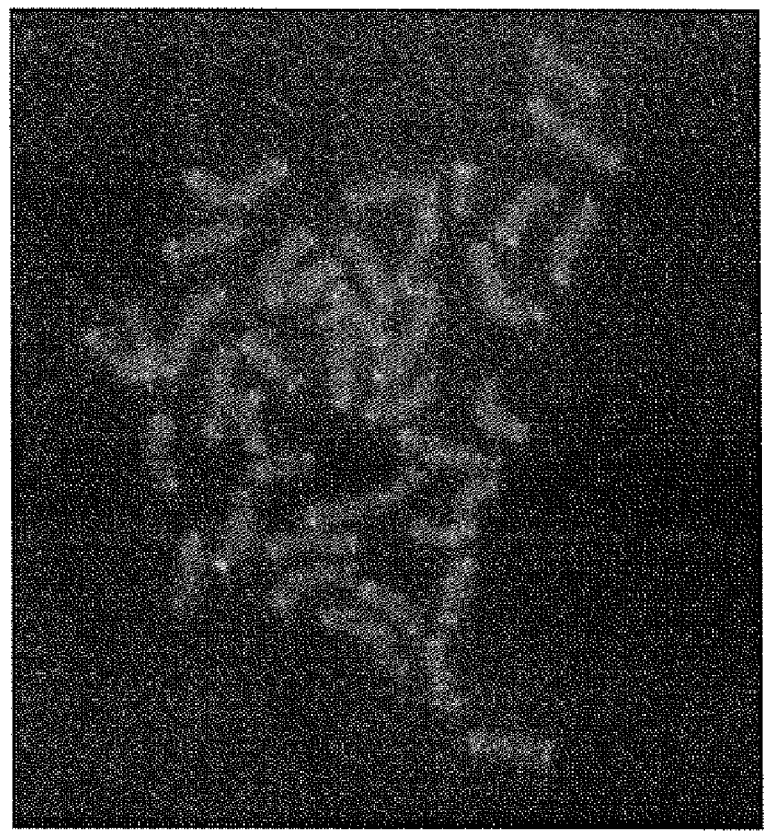
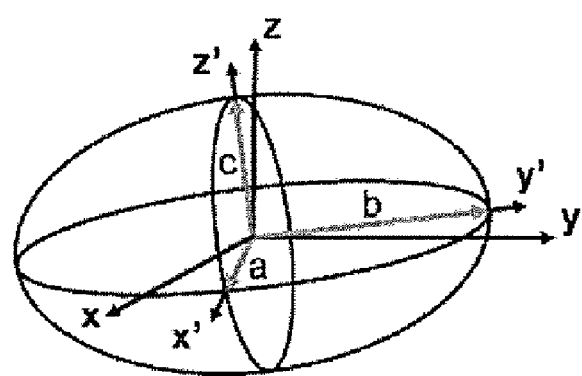
Figure 2

Figure 10

| | 2D | 3DF | 3DS |
|---|---|---|---|
| a | | | |
| b | | | |
| c | | | |
| d | | | |
| e | | | |
| f | | | |
| g | | | |
| h | | | |

- 4HT                     +4HT

Day 0

Day 1

Day 3

Day 10

A

B

METHOD OF MONITORING GENOMIC INSTABILITY USING 3D MICROSCOPY AND ANALYSIS

FIELD OF THE INVENTION

The present invention relates to methods for monitoring and determining genomic instability of a cell, in particular for the detection, monitoring and diagnosis of cell proliferative disorders such as cancer. In addition, the invention relates to three-dimensional analysis, and more specifically to characterization of the organization of telomeres and chromosomes.

BACKGROUND OF THE INVENTION

Telomeres are the ends of chromosomes. By capping the chromosomes, they are responsible for chromosomal integrity to prevent genomic instability[1-3]. Telomeres have been previously found at the nuclear edge[4], at the nuclear periphery[5], throughout the entire nucleus[6], in non-Rabl association[7], and in association with the nucleolus[8]. Similarly, the nuclear organization of chromosomes has been described as non-random[9-13] or random[14], based on two-dimensional (2D) imaging, three-dimensional (3D) reconstitution and mathematical modeling[15]. Organized territories of individual chromosomes have been observed in human[10-13], chicken[16] and plant[17]. A regular nuclear organization has also been described for replication and transcription[18-21]. While all this points to a well-defined nuclear organization, studies on radiation-induced aberrations suggested a random chromosomal organization[14].

At present, there is inexact knowledge about the 3D organization of either telomeres or chromosomes in interphase nuclei of normal, immortalized or tumor cells. However, this knowledge is of fundamental importance to the structural and functional organization of the normal nucleus and to the puzzle of genomic instability in tumor cells.

SUMMARY OF THE INVENTION

Using high resolution deconvolution microscopy and imaging, the present inventors have elucidated the three-dimensional (3D) organization and localization of telomeres and chromosomes in 3D interphase nuclei of normal, immortalized and tumor cells. It has been established that, independent of species and cell type, the mammalian telomeres and chromosomes are organized dynamically and non-randomly in the 3D nucleus of normal cells. On the other hand, 3D nuclei from tumor cells display a new order of telomeric and chromosome organization including telomere aggregations and concomitantly, altered positioning of telomeres and chromosomes. This altered nuclear telomeric organization allows chromosomal rearrangements. The precise organization of the 3D genome or alterations thereof reflects the differences in genomic stability vs instability of normal vs. cancer cells.

Accordingly, the present invention relates to a method of monitoring or detecting genomic instability in a test cell comprising:
(a) providing a sample comprising the test cell;
(b) characterizing telomeric and/or chromosomal organization in the test cell using three-dimensional (3D) analysis; and
(c) comparing the telomeric and/or chromosomal organization in the test cell with that of a control cell wherein a change in telomeric and/or chromosomal organization in the test cell compared to the control cell indicates the presence of genomic instability in the test cell.

The method of the invention may be used to detect or monitor disease, radiation and environmental exposure, and DNA repair and response in a cell. In particular the method of the invention may be used to detect, monitor or diagnose cancer. In addition, the method of the invention may be used to monitor disease treatment, in particular cancer treatment.

In addition, a method and system for characterizing the 3D organization of telomeres and/or chromosomes are described herein. The system includes an input module for inputting image data of the 3D organization of telomeres and/or chromosomes and a characteristic module for finding a parameter of the 3D organization therefrom.

Several such parameters may be used to characterize the 3D organization of telomeres and/or chromosomes. These parameters include a set of distances of the telomeres and/or chromosomes to a closest plane, the average of this set and the standard deviation of this set. Another parameter involves specifying the geometrical shape that best encompasses the organization of telomeres and/or chromosomes. The volume, intensity and shape of each the telomeres and/or chromosomes may also be used to characterize the 3D organization.

Each of these parameters to characterize the 3D organization of telomeres and/or chromosomes may be used for several purposes, including to monitor or detect genomic instability in a cell, to monitor, detect or diagnose a disease, such as cancer, and to monitor disease treatment, such as cancer treatment.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 illustrates a metaphase plate prepared from fetal liver cells directly isolated from 10 day old mouse embryos. Metaphase chromosomes and spreads were prepared and hybridized with PNA-telomeric probe that was Cy3 labeled.

FIG. 2 describes the volume spanned by the telomeres in an interphase nucleus as an ellipsoid. In general, the ellipsoid main axes along the x'y'z' axes do not coincide with the slide plane and optical axes of xyz. Also, in most of the cases the x'y' axes of the ellipsoid are approximately the same, a=b. Therefore, the ratio a/c is a good measure of the oblation level of the ellipsoid and of the telomere organization inside the nucleus.

FIG. 10 illustrates the telomere organization in interphase nuclei of mouse and human normal, immortalized and tumor cells. Telomeres are shown in 2D and 3D, for abbreviations see FIG. 4A. The following cell types are shown: a and b mouse embryonic fibroblast; c fibroblast; d VH primary human fibroblast; e HaCaT human keratinocyte cell line; f SH-EP neuroblastoma cell line; g cervical cancer; and h RAJI Burkift Lymphoma cell line.

Figure 3:
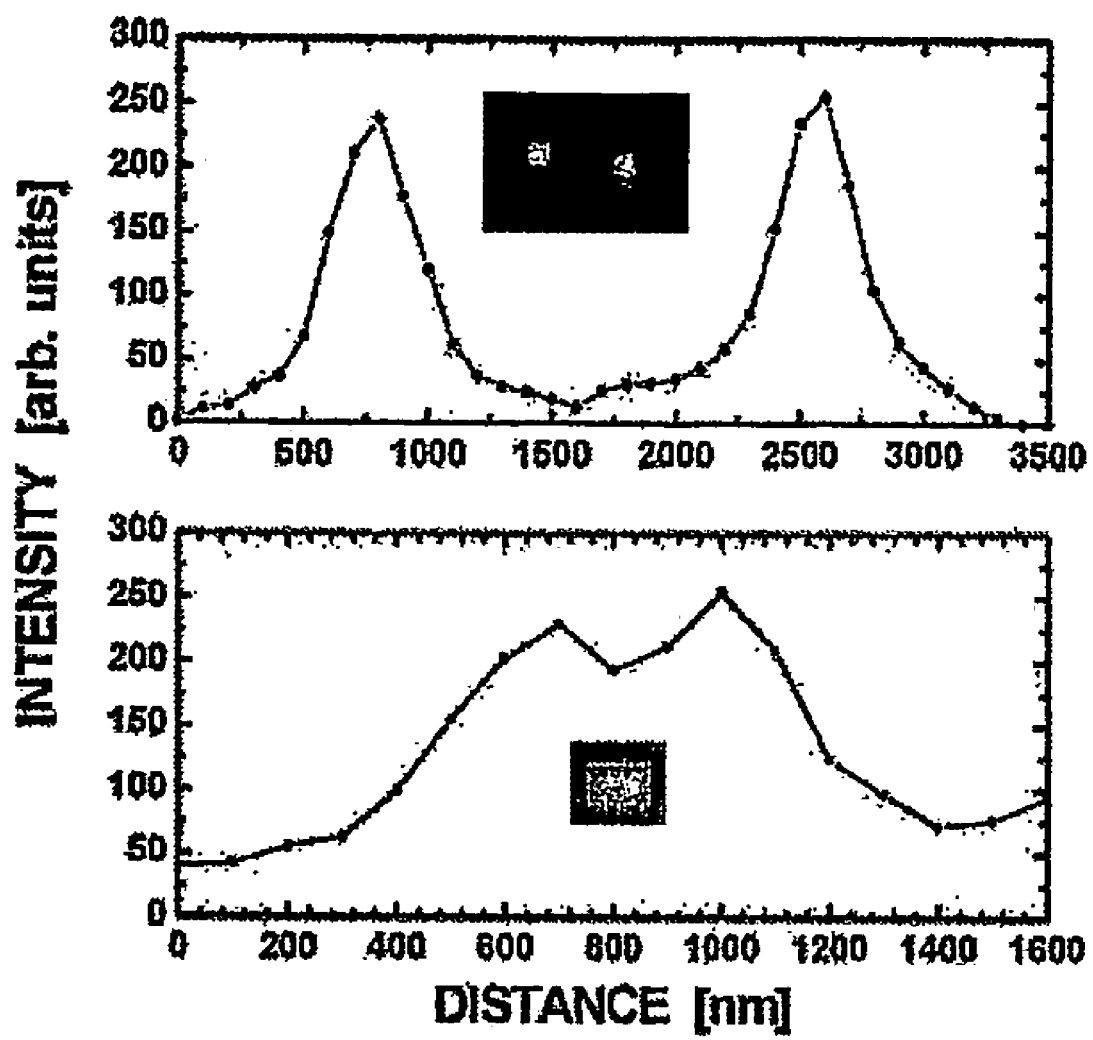
FIG. 3 illustrates the signal to noise and spatial resolution of the instruments used by the inventors. The fluorescence intensity in the measurements is bright and significantly higher than the background noise (typical signal to noise ratio of 10:1 or higher). This high signal to noise ratio enables a reliable analysis of the telomeres position and intensities. A pair of telomeres from an interphase nucleus was selected from a single plane from the stack of ~80 sections. Top: shows a pair of telomeres that are 1200 nm apart and can be easily separated. Bottom: shows a pair of telomeres that are 400 nm apart. The inserts show the actual image of the pairs.

DETAILED DESCRIPTION OF THE INVENTION (i) Method of Determining Genomic Instability The data presented herein shows that the multi-stage process of cellular transformation is one mechanism that triggers the re-organization of the ordered composition of telomeres and chromosomes within the 3D nuclear space. This is due to the telomere dysfunction associated with tumor development and genomic instability[22,23]. Genomic instability is a complex process through which the genome of the affected cell becomes prone to transformation and ultimately transformed, and involves the genetic reorganization of the cellular genome. As established herein, such genetic reorganization is readily observed in the 3D interphase nucleus, irrespective of the cell and tumor type. It is clearly visible when analyzing the 3D telomeric organization. Moreover, genomic instability also becomes apparent when examining the territories occupied by individual chromosomes and the chromosomal alignment along the telomeric disk (see below). The 3D intranuclear space and organization of telomeres and chromosomes are clearly abrogated in tumor cells. Instead, a new order of complexity is generated in which genetic rearrangements become feasible through the illegitimate juxtaposition of genetic material that is otherwise found in different regions of the nucleus. Thus, based on the present findings, it is now possible to reliably examine the presence or absence of genomic instability in interphase nuclei and to examine the generation of genomic instability over time. Such new avenues will impact on cancer biology, genetics and diagnostic innovations in medicine.

The present inventors have used high resolution deconvolution microscopy and imaging to elucidate the three-dimensional (3D) organization of telomeres and chromosomes in the interphase nuclei of normal, immortalized and tumor cells. It has been found that telomeres and chromosomes from tumor cells form an altered organization, occupying a 3D space that differs from their normal counterparts.

Accordingly, the present invention relates to a method of monitoring or detecting genomic instability in a test cell comprising:
  (a) providing a sample comprising the test cell;
  (b) characterizing telomeric and/or chromosomal organization in the test cell using three-dimensional (3D) analysis; and
  (c) comparing the telomeric and/or chromosomal organization in the test cell with that of a control cell wherein a change in telomeric and/or chromosomal organization in the test cell compared to the control cell indicates the presence of genomic instability in the test cell.

As used herein, the term 'cell' includes more than one cell or a plurality of cells or portions of cells. The sample may be from any animal, in particular from humans, and may be biological fluids (such as blood, serum, saliva or cerebrospinal fluid), tissue, hair or organ. An advantage of the method of the present invention is that only a very thin slice or section of a tissue (even thinner than the width of a cell) can be used in the method.

In embodiments of the invention the "test cell" is a cell that is suspected of having a cell-proliferative disorder such as cancer. In such an embodiment, the test cell includes, but is not limited to, a cancer cell. The term cancer includes any cancer including, without limitation, cervical cancer, ovarian cancer, pancreatic cancer, head and neck cancer, squamous cell carcinoma, gastrointestinal cancer, breast cancer (such as carcinoma, ductal, lobular, and nipple), prostate cancer, non small cell lung cancer, Non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, colon cancer, plasmacytoma, head and neck squamous cell carcinoma, lymphoma, and cMyc-dependent tumors. In a preferred embodiment, the cancer includes, without limitation, colon cancer, neuroblastoma, plasmacytoma, head and neck squamous cell carcinoma, lymphoma, breast cancer and cMyc-dependent tumors. When using cancer cells as the test cell, the sample can be any sample that contains the cancerous cells such as a biopsy from the tumor or blood.

As used herein, the term "control cell" refers to a normal, disease-free cell.

The term "three-dimensional (3D) analysis" as used herein refers to any technique that allows the 3D visualization of cells, for example high resolution deconvolution microscopy. In an embodiment of the invention, the 3D analysis is performed using the system described hereinbelow.

The term "telomeric and/or chromosomal organization" as used herein refers to the 3D arrangement of the telomeres and/or chromosomes during any phase of a cell cycle and includes such parameters as telomere and/or chromosome size, alignment, state of aggregation and the size of the 3D space that the telomeres and/or chromosomes occupy. "Telomere organization" also refers to the size and shape of the telomeric disk which is the organized structure formed when the telomeres condense and align during the late G2 phase of the cell cycle. The term "state of aggregation" refers to the size and shape of the aggregates of telomeres and/or chromosomes.

The "change in telomeric and/or chromosomal organization in the test cell compared to the control cell" may be determined, for example by counting the number of telomeres in the cell, measuring the size of any telomere or telomere aggregate or characterizing 3D chromosomal organization during any phase of the cell cycle. In an embodiment of the invention, if any telomere in the test cell is larger (i.e. form more aggregates), for example double the size, of those in the control cell, then this indicates the presence of genomic instability in the test cell. The telomeres in a test cell with genomic instability may also be fragmented and therefore appear smaller than those in the control cell. In further embodiments, the change in telomeric organization in the test cell compared to the control cell is determined by monitoring the alignment of telomeres in the telomeric disk during the late G2 phase of the cell cycle as well as the size of the telomeric disk during the late. G2 phase. The telomeres in a cell with genomic instability will fail to align in the way those in a control cell will align, and therefore the telomeric disk in cells with genomic instability will be distorted and occupy an enlarged space compared to controls. In still further embodiments of the present invention, a change in chromosomal organization, positioning or alignment in the test cell compared to the control cell indicates the presence of genomic instability in the test cell. For example, the intermingling of genetic material is indicative of genomic instability. In another embodiment of the invention, a change in telomeric and/or chromosomal organization in the test cell compared to the control cell may be determined by comparing parameters used to characterize the organization of telomeres and/or chromosomes. In a further embodiment, such parameters are determined or obtained using a system and/or method described hereinbelow.

The results obtained in the present studies show that genomic instability in a cell is correlated with disease. In an embodiment of the invention, the presence of genomic instability in a cell, as determined using the method of the present invention, indicates the presence of a cell proliferative disorder in the cell. Therefore in an embodiment of the present invention the method the presence of genomic instability in a cell is indicative of a cell proliferative disorder. In particular, the presence of genomic instability in a cell, as determined using the method of the present invention, indicates that the cell is a cancer cell. Therefore in an embodiment of the present invention the method the presence of genomic instability in a cell is indicative of cancer.

Accordingly, the present invention also includes of method of detecting, monitoring disease in a test cell comprising:
(a) providing a sample comprising the test cell;
(b) characterizing telomeric and/or chromosomal organization in the test cell using three-dimensional (3D) analysis; and
(c) comparing the telomeric and/or chromosomal organization in the test cell with that of a control cell wherein a change in telomeric and/or chromosomal organization in the test cell compared to the control cell indicates the presence of disease in the test cell.

In an embodiment of the invention, the disease is a cell proliferative disorder, for example, cancer. The cancer includes breast cancer, prostate cancer, lymphoma, leukemia, sarcoma, melanoma, head and neck squamous cell carcinoma, lung cancer, ovarian cancer and endometrial cancer.

The method of the invention may also be used to monitor disease treatment. For example, samples comprising test cell(s) from a patient with a cell proliferative disorder may be taken at various time points, for example before, during and after chemo or other forms of therapy, and the presence of genomic instability determined. The diminishing of genomic instability in the test cells over time would be indicative of successful therapy. Conversely, an increase in or lack of change in the genomic instability of the test cells over time would be indicative of unsuccessful therapy.

Accordingly, the present invention further relates to method of monitoring disease treatment in a test cell comprising:
(a) providing a sample comprising the test cell;
(b) characterizing telomeric and/or chromosomal organization in the test cell using three-dimensional (3D) analysis; and
(c) comparing the telomeric and/or chromosomal organization in the test cell with that of a control cell wherein a change in telomeric and/or chromosomal organization in the test cell compared to the control cell is correlated with disease treatment in the test cell.

In addition, the method of the invention may be used to monitor radiation, environmental impact, injury and key proteins in DNA repair in a cell.

Accordingly, the present invention further relates to method of monitoring radiation, environmental impact, injury and key proteins in DNA repair in a test cell comprising:
(a) providing a sample comprising the test cell;
(b) characterizing telomeric and/or chromosomal organization in the test cell using three-dimensional (3D) analysis; and (c) comparing the telomeric and/or chromosomal organization in the test cell with that of a control cell wherein a change in telomeric and/or chromosomal organization in the test cell compared to the control cell is correlated with radiation, environmental impact, injury or DNA repair in the test cell.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

In addition, the present invention relates to a method of monitoring or detecting genomic instability in a test cell comprising:
(a) characterizing telomeric and/or chromosomal organization in the test cell using three-dimensional (3D) analysis; and
(b) comparing the telomeric and/or chromosomal organization in the test cell with that of a control cell wherein a change in telomeric and/or chromosomal organization in the test cell compared to the control cell indicates the presence of genomic instability in the test cell.

The present invention also includes of method of detecting, monitoring disease in a test cell comprising:
(a) characterizing telomeric and/or chromosomal organization in the test cell using three-dimensional (3D) analysis; and
(b) comparing the telomeric and/or chromosomal organization in the test cell with that of a control cell wherein a change in telomeric and/or chromosomal organization in the test cell compared to the control cell indicates the presence of disease in the test cell.

The present invention further relates to method of monitoring disease treatment in a test cell comprising:
(a) characterizing telomeric and/or chromosomal organization in the test cell using three-dimensional (3D) analysis; and
(b) comparing the telomeric and/or chromosomal organization in the test cell with that of a control cell wherein a change in telomeric and/or chromosomal organization in the test cell compared to the control cell is correlated with disease treatment in the test cell.

(ii) System for Characterizing 3D Organization of Telomeres and/or Chromosomes

The present invention relates to methods and systems for characterizing the 3D organization of telomeres and/or chromosomes.

Figure 19:
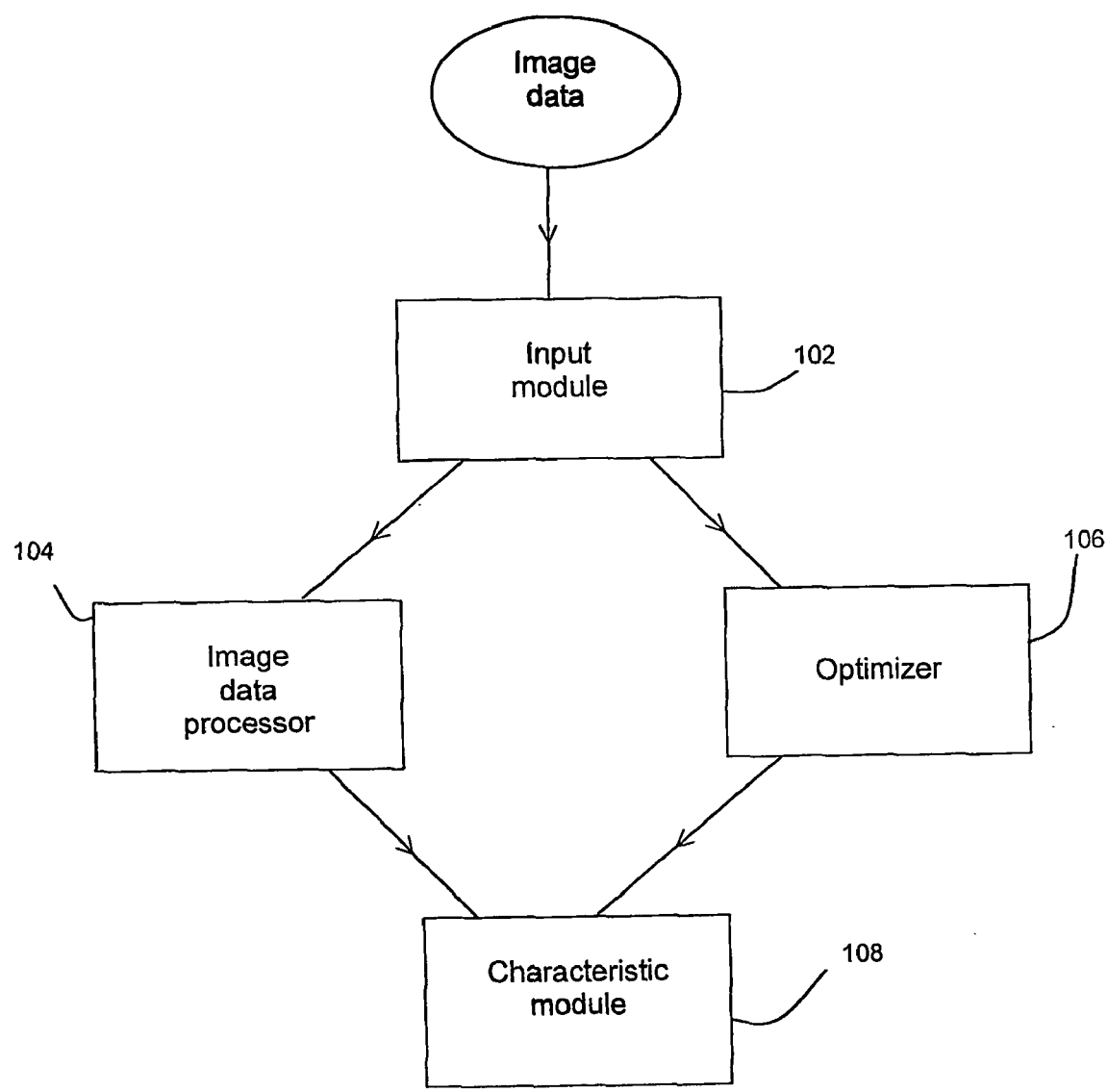
FIG. 19 is a block diagram of a system for characterizing a 3D organization of telomeres and/or chromosomes in interphase nuclei.

FIG. 19 shows a block diagram of a system 100 for characterizing a 3D organization of telomeres and/or chromosomes. The system 100 includes an input module 102, an image data processor 104, an optimizer 106 and a characteristic module 108.

The input module 102 inputs image data of the 3D organization of telomeres and/or chromosomes. The input module 102 includes appropriate hardware and/or software, such as a CD-ROM and CD-ROM reader, or other data storage and reading means. The inputting performed by the input module 102 need not be from outside the system 100 to inside the system 100. Rather, in some embodiments, the inputting of data may describe the transfer of data from a permanent storage medium within the system 100, such as a hard disk of the system 100, to a volatile storage medium of the system 100, such as RAM.

The image data can be obtained using regular or confocal microscopy and can include the intensities of one or more colors at pixels (totaling, for example, 300×300 or 500×500) that comprise an image of a nucleus. The image data can also be grey level image data of a nucleus that has been appropriately stained to highlight telomeres and/or chromosomes. Several images (on the order of 100) are obtained corresponding to slices along a particular axis. Thus, the image data may correspond to a total of about $2.5 \times 10^7$ pixels. In one embodiment, the slices may be on the order of 100 nanometers apart. In this manner, the image data accounts for the 3D quality of the organization of telomeres and/or chromosomes. In addition, the confocal microscope is able to obtain the intensity of two colors, for example blue and green, of the nucleus at every pixel imaged, thereby doubling the amount of data points.

To obtain an image of telomeres and/or chromosomes, a stain such as DAPI can be used to preferentially mark the heterochromatin material that comprises DNA. A second stain, such as cy3, together with an appropriate label, such as PNA telomere probe, can be used to mark the telomeric portion of the heterochromatin material.

To improve the quality of the image data, various techniques can be brought to bear as known to those of ordinary skill, such as constrained iterative deconvolution of the image data to improve resolution. Such constrained iterative deconvolution may not be required if confocal, instead of regular, microscopy is used as the image data may be of superior resolution. In addition, other instruments, such as an apotome, may be used to improve the quality of the image.

The image data processor 104 processes the image data to find a set of coordinates $\{(x_i, y_i, z_i)\}$, i=1, ..., N, where $(x_i, y_i, z_i)$ is a position of the ith telomere. For this purpose, the image data processor 104 identifies "blobs" within the image data that can be identified as a telomere and/or chromosome using a segmentation process. Each blob identified as a telomere and/or chromosome has a non-negligible volume (for example, a small telomere may have a volume of 4×4×4 pixels, a large one a volume of 10×10×10, where the size of the nucleus may be approximately 200×200×100 pixels). There is some freedom, therefore, in choosing "the position" of the telomere and/or chromosome. One possibility is to choose for this position the center of gravity of the telomere and/or chromosome, or more generally, the telomere and/or chromosome organization.

The optimizer 106 finds a plane $P^{min}$ that is closest to the set of coordinates. To find the closest plane, the distance $D_i$ between the location of the ith telomere, $(x_i, y_i, z_i)$, and the plane given by $ax+by+cz=0$ is considered:

$$D_i = \frac{ax_i + by_i + cz_i}{\sqrt{a^2 + b^2 + c^2}}$$

The optimizer 106 finds the parameters a,b,c,d that minimize the function.

$$\sum_{i=1}^{N} D_i(a, b, c, d).$$

The characteristic module 108 proceeds to find at least one parameter that can be used to characterize the 3D organization of telomeres and/or chromosomes. "Parameters used to characterize the organization of telomeres and/or chromosomes" include:

1) A set of distances $\{d_i\}$, i=1, . . . , N, where $d_i$ is the distance between $(x_i, y_i, z_i)$ and the plane $P^{min}$. 2) $\bar{d}$ and $\sigma$, the average distance and standard deviation of the set of distances $\{d_i\}$:

$$\bar{d} = \frac{1}{N} \sum_{i=1}^{N} d_i,$$

and $$\sigma^2 = \sum_{i=1}^{N} \frac{(d_i - \bar{d})^2}{N}, \text{ respectively.}$$

3) A three dimensional geometrical shape that best encompasses the 3D organization. For example, the geometrical shape can be the ellipsoid, having principal axes $\alpha_1$, $\alpha_2$, and $\alpha_3$, that best encompasses the 3D organization of the telomeres and/or chromosomes. Several definitions of "best encompasses" can be used. For example, the ellipsoid that best encompasses the telomeres can be defined as the ellipsoid of smallest volume that encloses a certain fraction (e.g., 100%) of the telomeres. If a set of more than one ellipsoid fulfills this condition, other restrictions can be used to reduce the set to just one ellipsoid, such as further requiring the ellipsoid to have the smallest largest ratio of principle axes (i.e., the "most circle-like" ellipsoid). It should be understood that other definitions of "best encompasses" the telomeres and/or chromosomes can be used.

It has been observed that the ellipsoid that best encompasses the telomeres often approximates an oblate spheroid with $\alpha_1$ approximately equal to $\alpha_2$. In such case, it is sufficient to specify just $\alpha_2$ and $\alpha_3$. Alternatively, an oblateness ratio, $\alpha_3/\alpha_1$ or $\alpha_1/\alpha_3$, can be used to characterize the oblate spheroid describing the organization of the telomeres.

4) A set of volumes $\{V_i\}$, where $V_i$ is the volume of the ith telomere.

5) A set of three dimensions $\{(Dx_i, Dy_i, Dz_i)\}$, i=1, . . . , N, where $(Dx_i, Dy_i, Dz_i)$ are principle axes of an ellipsoid describing the ith telomere.

6) A set of intensities $\{I_i\}$, i=1, . . . , N, where $I_i$ is the total intensity of the ith telomere. (In other embodiments, instead of the total intensity, the average intensity of each telomere can be computed.) That is, if the ith telomere is associated with K pixels, then $$I_i = \sum_{j=1}^{K} I_{i,j}$$

where $I_{i,j}$ is the intensity of the jth pixel of the ith telomere.

Figure 20:
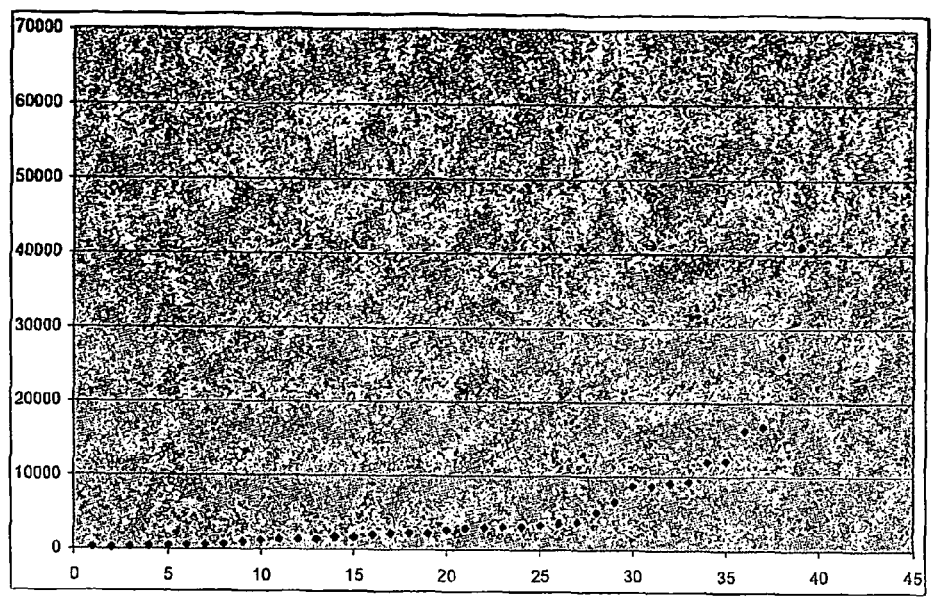
FIGS. 20A and 20B show plots of intensities of telomeres of interphase nuclei that may be used to characterize a 3D organization of telomeres.
Figure 20:
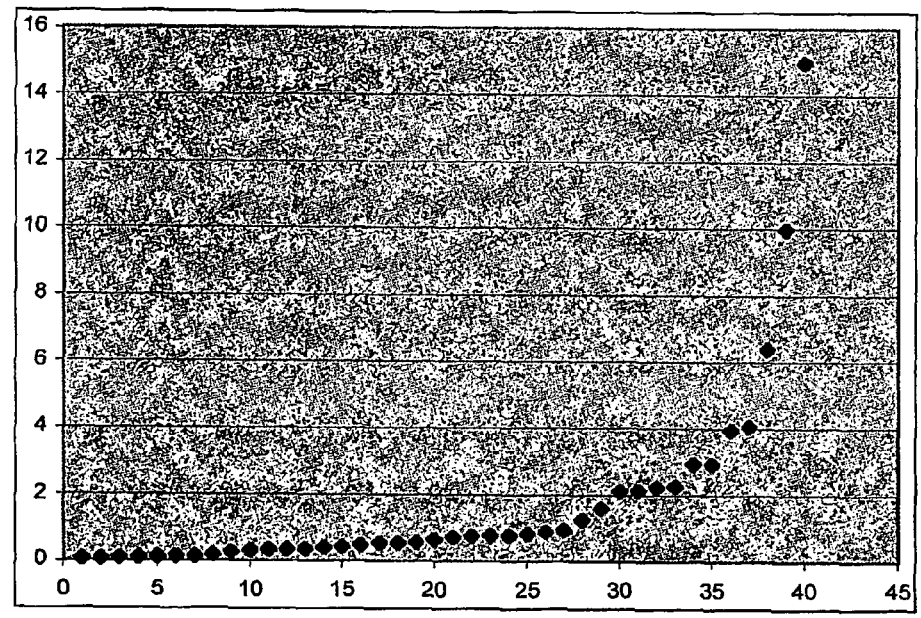

FIG. 20A shows a plot of i, where i denotes the ith telomere, versus $I_i$, where the ordering of the telomeres, from left to right, is from lowest total intensity to highest total intensity. FIG. 20B shows a similar plot except that the vertical axis is $I_i$ divided by the average total intensity over a sample set of cells.

In the last three cases, the sets can be used to calculate statistical measures such as an average, a median or a standard deviation.

The parameters 1-5 outlined above characterize the 3D organization of the telomeres and/or chromosomes by focusing on the geometrical structure of the telomeres and/or chromosomes. Parameters 1 and 2 are motivated by the finding that, especially during the late G2 phase of the cell cycle, telomeres tend to lie on a plane. Parameters 1 and 2 measure deviations of telomeres from a planar arrangement.

Parameter 3 attempts to describe, with features, such as the three principal axes of an ellipsoid or the oblateness ratio, the overall shape of the 3D organization. While parameters 1-3 are global geometric characteristics, dealing with the overall shape of the organization parameters 4 and 5 are local geometric characteristics in the sense that they involve the geometry of each individual telomere.

The final parameter is also local, involving the intensity of each individual telomere.

As stated above, the characterizations of the 3D organization of telomeres and/or chromosomes can be used for a number of purposes. For example, by comparing a parameter to a standard value, diseases may be monitored or diagnosed, as described above. The standard (control) values can arise from population studies, theoretical models, or the characterization of control cells. In addition, the characterizations of the 3D organization of telomeres and/or chromosomes can be used to monitor or detect genomic instability in a cell.

The following non-limiting examples are illustrative of the present invention:

EXAMPLES

Example 1

3D Organization of Telomeres and Chromosomes in the Nucleus of Mammalian Cells

Methods

Cells

Table 1 summarizes the cells that were used in this study. Mouse primary cells were directly isolated from BALB/c mice. Human primary cells were obtained form healthy donors. Cell lines and culture conditions have been described elsewhere (HaCaT[25], Pre-B[26], BAF3[27] Colo320DM[28], SH-EP[29]) The primary plasmacytoma DCPC21 was isolated from a BALB/c mouse[30]. Head and neck squamous cell carcinoma and control tissue were obtained from a patient at CancerCare Manitoba upon ethics approval and informed consent.

Fixation Techniques.

Cells were fixed in four ways: i) following cytospin preparations, cells were fixed in 3.7% formaldehyde (1×PBS/50 mM MgCl$_2$), ii) cells were allowed to grow on glass slides and were fixed in 3.7% formaldehyde, iii) cells were fixed in suspension with 3.7% formaldehyde, and iv) cells were fixed in methanol:acetic acid (3:1) according to standard protocols[31]. Tissue was fixed following cryosection (5 mm sections were used) in 3.7% formaldehyde (1×PBS/50 mM MgCl$_2$).

Fluorescent Activated Cell Sorter (FACS) Analysis.

For FACS analysis, primary lymphocytes were fixed in 70% ethanol and stained with propidium iodide (1 µg/ml) following RNAse (20 µg/ml) digestion. FACS profiles were obtained at 0, 24, 48, and 69 hours post stimulation.

Cell Sorting.

Cells were stained with Hoechst 33342 (Molecular Probes) at a final concentration of 1 µg/ml for 90 minutes at 37° C. and 5% of CO2. Cells were sorted according to their DNA content (G0/G1, S and late G2 phases).

BrdU Labeling.

Cells were in vivo labeled with 10 µM of BrdU (5-Bromo-2'-deoxyuridine, SIGMAALDRICHT, Lyon, France) for 1 hour at 37° C. in humidified atmosphere (5%CO2). BrdU was then detected with 5 µl/1×10$^6$ cells of anti-BrdU-FITC antibody (TEBU, Le Perray-en-Yvelines, France) at the identical conditions for 30 minutes. Thereafter, all BrdU (i.e. FITC)-positive cells were live sorted, placed into culture for different times and harvested at 3.5, 4, 5, 6, 7, 8, 8.5, 9 and 10 hours after labeling and sorting. Then, the cells were fixed for 3D analysis. A minimum of 20 nuclei were imaged and analyzed for each time point. The fraction of nuclei with a TD was measured, in mitosis as well as interphase nuclei without TD and mitotic figures that were evaluated as G1 and S phase cells.

Telomere FISH Using Cy3-labled PNA Telomere Probes (DAKO, Denmark).

Telomere FISH was performed as described[32] using a Cy3 labeled PNA telomere probe (DAKO, Glostrup, Denmark). Telomere hybridizations were specific as shown by metaphase hybridizations and the correct number of the telomeric signals observed at the ends of chromosomes prepared from primary cells (FIG. 1).

Chromosome Painting and Spectral Karyotyping.

Chromosome painting was carried out according to standard protocols[31] using a chromosome 11 paint from CedarLane (Hornby, ON, Canada), and chromosome 1 and 21 paints from MetaSystems Group Inc. (Boston, Mass., USA). Spectral karyotyping was carried out as described[30] using the mouse SKY kit from Applied Spectral Imaging Inc. (Carlsbad, Calif., USA).

Image Acquisition and 3D Analysis.

If not stated otherwise, a minimum of 20 cells and a maximum of 30 cells were analyzed by 3D imaging using Axioplan 2 (Zeiss) with 100 W fluorescence, a cooled AxioCam HR B&W with 1× adaptor (Zeiss). DAPI, FITC and Cy3 filters (Zeiss) were used in combination with Planapo 63×/1.4 oil (Zeiss). Axiovision 3.1 software with deconvolution module and rendering module were used (Zeiss). 80 and 160 sections were acquired at 100 and 200 nm respectively. The constrained iterative algorithm option was employed[33] and surfaces rendered in x, z and x, y axes. The total nuclear volume (sphere) was calculated using the following formula; $v=(4\pi/3)r^3=(\pi/6)d^3$. The volume of the segment of the 3D nuclear sphere was calculated using the following formula: $v=(\pi/6)(3r_1^2+3r_2^2+h^2)h$, with radius of the sphere: r, radii of bases: $r_1, r_2$, height: h, volume: v, diameter: d.

Telomere Organization in the 3D Nucleus.

For quantitative analysis of the telomere organization inside the nucleus, was convenient to describe the volume occupied by the telomeres as an ellipsoid (three different main axes, FIG. 2) but the organizations were almost without exception found to be oblate or spherical (i.e. the two principle axes along the main x'y' plane of the spheroid are similar). The volume can be conveniently described as an ellipsoid having two axes of equal length[34]. As such, it is simpler to describe the spheroid degree of variation from a perfect sphere by the ratio a/c where a=b are the similar semi-axes and c is the third one. Such a description reflects the degree to which the telomere volume is oblate. As an example, a perfect sphere will have a/c=1 ratio while an oblate volume will have a ratio of a/c>1. The x'y' plane of the spheroid should not necessarily be parallel to the microscope slide plane (described by xy), especially in those cases where tissue section are analyzed.

Results

Resolution.

The optical resolution and signal to noise ratio (SNR) are shown in FIG. 3A. The images of two neighbor telomeres that are 1200 nm and 400 nm apart and the corresponding intensity along the line connecting the pair indicates the smallest telomere distance that can still be unambiguously distinguished. This optical resolution is good enough for studying the nuclear organization of the telomeres, even if close telomeres are indistinguishable.

Cell Types.

Figure 4:
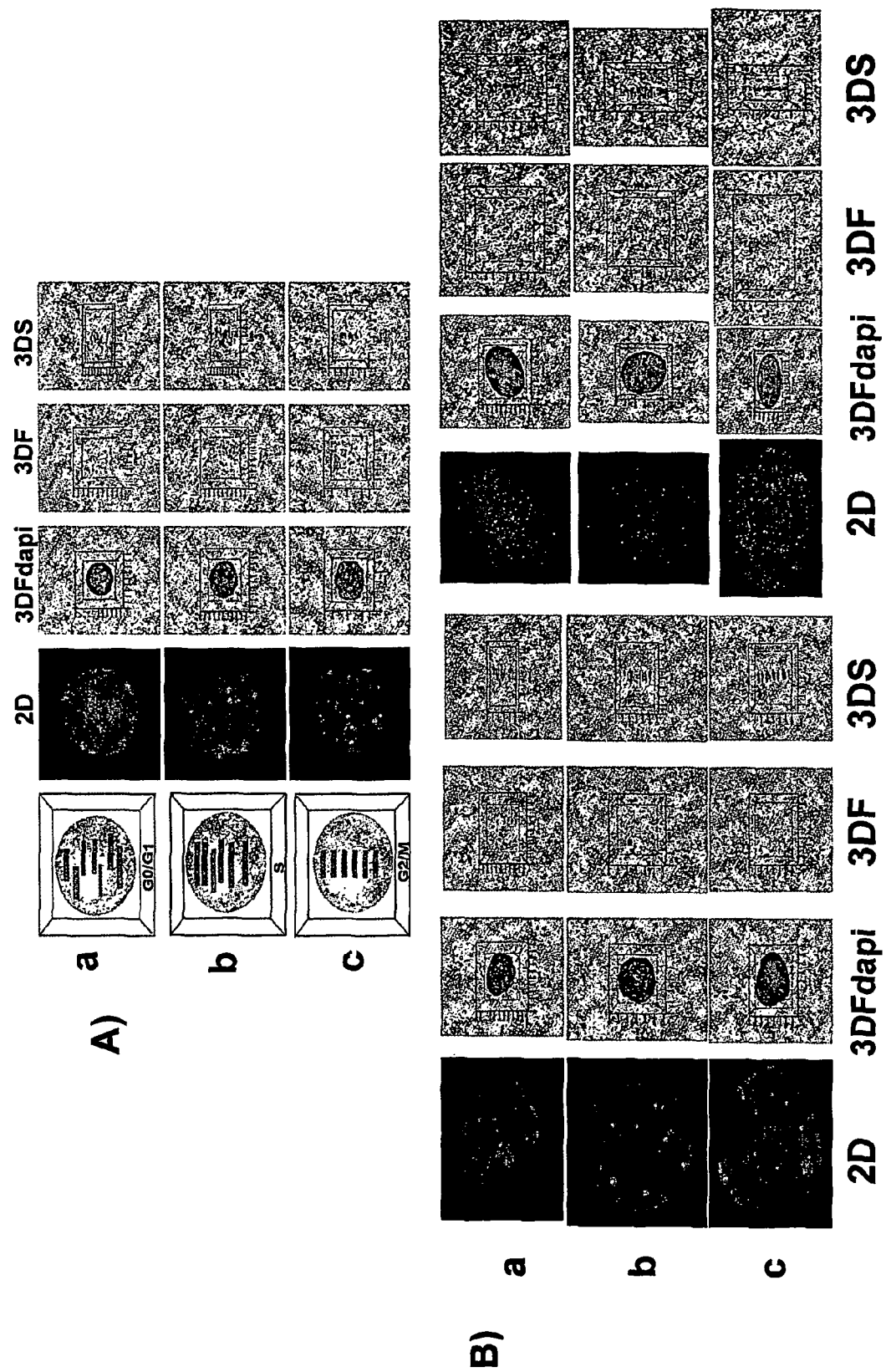
FIG. 4 illustrates telomere organization in interphase nuclei of primary mouse and human cells. 4A. Telomere organization in primary mouse lymphocytes. a-c Localization of telomeres in primary BALB/c splenic B lymphocytes maintained in the presence (b,c) or absence (a) of lipoploysaccharide (LPS) for a 0 hours, b 24 hours, c 69 hours. As indicated, each of the five panels illustrate; a schematic representation of the telomere localization, followed by the 2D image of the interphase nucleus and its telomeres, followed by the 3D front view of the nucleus with DAPI (blue) counterstain (3DFdapi), 3DF without DAPI (3DF), and the 3D side view of the telomeres within the nucleus (3DS). Telomeres are stained in red (Cy3 labeled PNA telomere probe). In each of the panels, the 3D interphase localization of the telomeres can be visualized as 3D movies (available from Dr. Sabine Mai, Manitoba Institute of Cell Biology, CancerCare Manitoba, University of Manitoba, 675 McDermot Ave., Winnipeg, Manitoba). Abbreviations: 3DF stands for three dimensional front view, and 3DS stands for three dimensional side view. 4B. Telomere organization in primary human cells. a-c Localization of telomeres in primary human lymphocytes stimulated with phytohemaglutinin (PHA) and in primary human fibroblasts (left and right panels respectively). As indicated, each of the panels show representative images in 2D, 3DFdapi, 3DF, and 3DS for decondensed (a), less decondensed (b) and condensed (c) telomeres (red). Abreviations as in FIG. 4A. In each of the panels, the 3D interphase localization of the telomeres can be visualized as 3D movies (available from Dr. Sabine Mai, Manitoba Institute of Cell Biology, CancerCare Manitoba, University of Manitoba, 675 McDermot Ave., Winnipeg, Manitoba).

The findings for primary cells (FIG. 1), immortalized cells (FIG. 2), and tumor cells and tissue (FIGS. 3 and 4) are summarized below. For all data, constrained iterative deconvolution of fluorescent images acquired at 200 nm sections through the entire nucleus was used. Different cell types and tissue of mouse and human origin were examined (Table 1). FIG. 1, with a simplified model on dynamic telomeric localization illustrates the data for primary mouse and human lymphocytes in both 2D and 3D formats. 3D images are presented from the three-dimensional front view (3DF) and from the three-dimensional side view (3DS). 3D movies were obtained that further illustrate the 3D findings. The 3D movies are readily available upon request from Dr. Sabine Mai, Manitoba Institute of Cell Biology, CancerCare Manitoba, University of Manitoba, 675 McDermot Ave., Winnipeg, Manitoba.

Telomeric Organization and the Cell Cycle.

As shown in FIGS. 4A and B, the telomeric organization is a dynamic cell cycle dependent process. The commonly used 2D-analysis does not allow for a precise localization of the telomeres within interphase nuclei. In contrast, 3D analysis defines their exact nuclear location. The 3D data demonstrate that telomeres are highly ordered in the nuclear space of primary cells. In resting, non-cycling (G0/G1) primary mouse and human lymphocytes, telomeres are decondensed. At this time, the segment of the nuclear sphere that telomeres occupy is found consistently within a 680 mm$^3$ nuclear region in a total nuclear volume of 905 mm$^3$ (FIG. 4A, panel a, and in 3D movies). The telomeres condense prior to late G2 and are then located within a volume of 410 mm$^3$ (FIG. 4A, panel b, and in 3D movies). The telomeres fully condense in late G2 and precisely align, forming an organized structure that has been designated the telomeric disk (TD) (FIG. 4A, panel c, and in 3D movies). In the TD, telomeres are evenly distributed throughout the disk. The TD occupies a 190 mm$^3$ volume of the central nuclear space (FIG. 4A, panel c, and in 3D movies). Similar results on telomeric organization were recorded in primary human lymphocytes (FIG. 4B), primary human fibroblasts (data not shown), and in normal human epithelial tissue (FIG. 5B, panels a and b). In summary, this dynamic process of telomeric organization is found in the 3D nuclear space of different cell types and species and thus appears to be the common rule governing the dynamics of nuclear organization during normal cell cycle.

One specific parameter of the method is the a/c ratio, which describes the level to which the volume occupied by the telomeres is oblate. The larger it is, the more oblate (or disk-like) is the shape of the volume occupied by the telomeres, while a/c=1 means that this volume is spherical.

By analyzing cell cycle sorted primary mouse lymphocytes the inventors found that the 3D telomere organization changes during the cell cycle. Telomeres are widely distributed throughout the nucleus in G0/G1 and S phases with a calculated a/c ratio of 0.9±0.4 which means a spherical-like volume. However, during G2, telomeres are not observed throughout the whole nucleus. Their 3D organization changes, with all the telomeres assuming a central structure that is herein called the telomeric disk (TD). This disk has never been reported before. In this ordered structure, all the telomeres align in the center of the nucleus as cells progress into late G2 phase. The a/c ratio they assume is 6.0±2.0.

Figure 5:
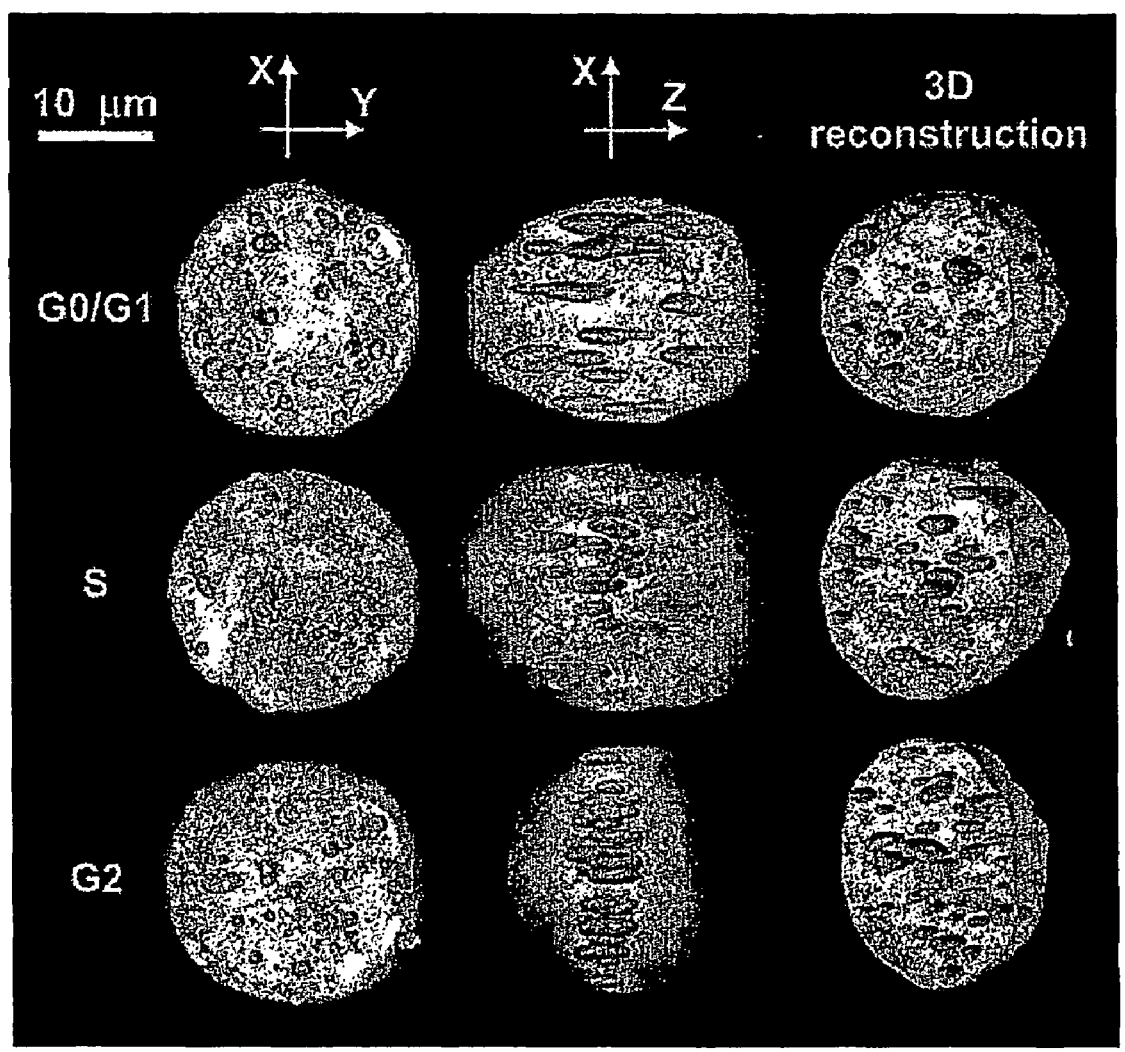
FIG. 5 illustrates the distribution of telomeres in the interphase nucleus of three typical cells selected from the G0/G1 phase (upper row), S phase (middle row) and late G2 phase (lower row). Each telomere distribution is shown from a top view (the XY plane) as observed along the optical axis Z (left column), from a side view (XZ plane) as observed along the Y axis (center column) and as a 3D image of the telomeres in an open nucleus (right column). When shown from the top and side views, the telomeres are displayed on top of the projected image of the nucleus. This projection demonstrates the extent of the chromatin (and therefore chromosomes) and defines the area and borderline of the nucleus.

Typical cells from different phases are shown in FIG. 5. The a/c ratio of these cells in G0/G1, S and late G2 phases is 0.8, 0.8 and 6 respectively and clearly shows the correlation of the a/c ratio with the telomere distribution and the organization of the TD that have been found in the G2 phase. The elongation of the telomeres along the Z axis relative to the XY plane has the same ratio as the point spread function of the present system and therefore is a result of the poorer optical resolution along the optical axis. This however, has a very small effect on the shape of the whole nucleus.

Figure 6:
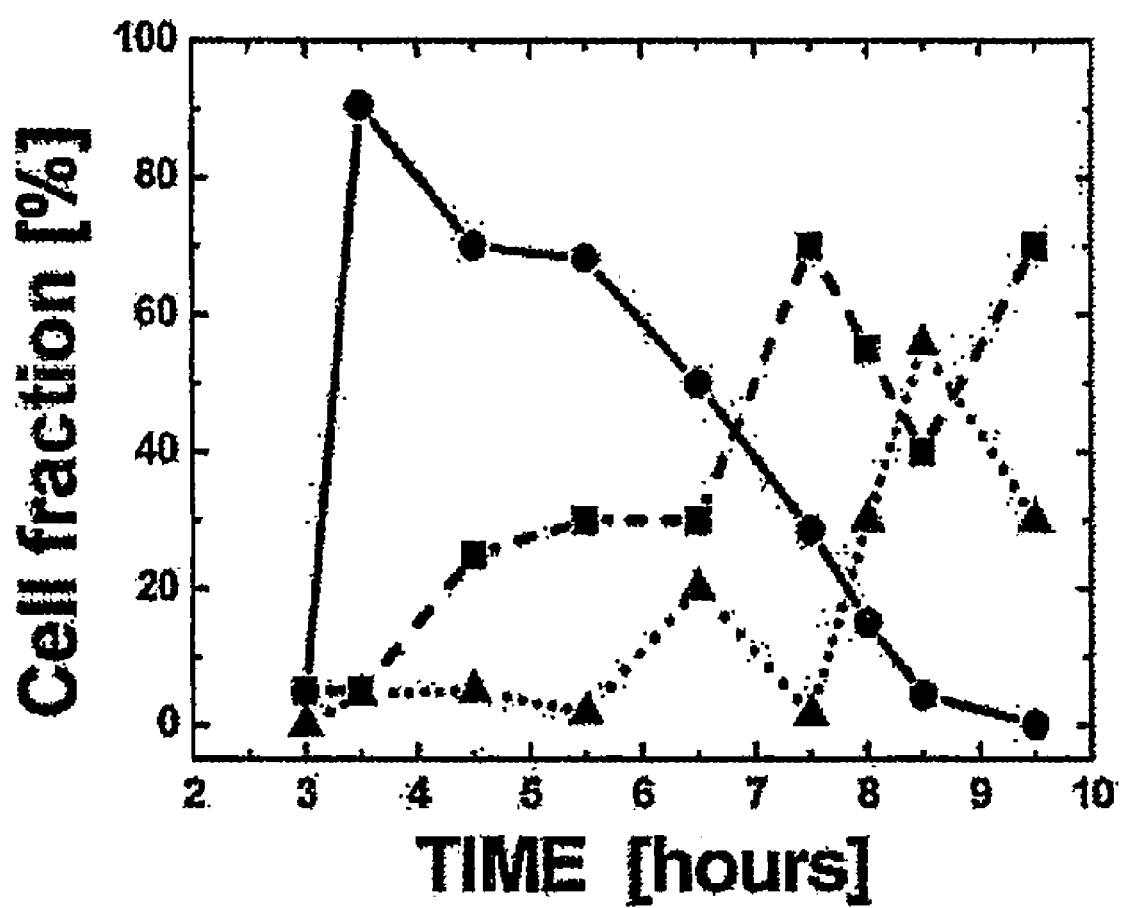
FIG. 6 illustrates cell fractions as a function of time showing the TD (black line and circles), entering mitosis (dashed line and squares) and entering G1 (dotted line and triangles). The time is measured since the population was harvested after being sorted. From the bar graph one can observe that most cells (90%) form a telomeric disk (TD) 3.5 hours after BrdU incorporation. The fraction of metaphase cells peaks at 7.5 hours (65%) and the number of interphase cells that does not have a TD (and are interpreted as being in G1 phase) peaks after 8.5 hours (57%). The increase in the number of metaphases at 9.5 hours can not be explained and probably lies within the limits of experimental errors. This demonstrates that a TD is formed in late G2 phase. As cells progress from G2 to M, telomeres start to spread out and the organization of telomeres into the TD is no longer observed. At the end of M phase, the inventors begin to observe nuclei in G1 conformation of telomeres with wide distribution of telomeres throughout a smaller nucleus.

To further study the phase transition timing along the cell cycle the synchronous BrdU sorting method was used. FIG. 6B shows the cell fractions as a function of time. Most cells (90%) form a TD 3.5 hours after BrdU incorporation. The fraction of metaphase cells peaks at 7.5 hours (65%) and the cell fraction of interphase cells that do not have a TD (and are interpreted as being in the G1 phase) peaks at 8.5 hours (57%).

Telomeric Organization in Immortalized Cells and Tumor Cells.

Figure 10:
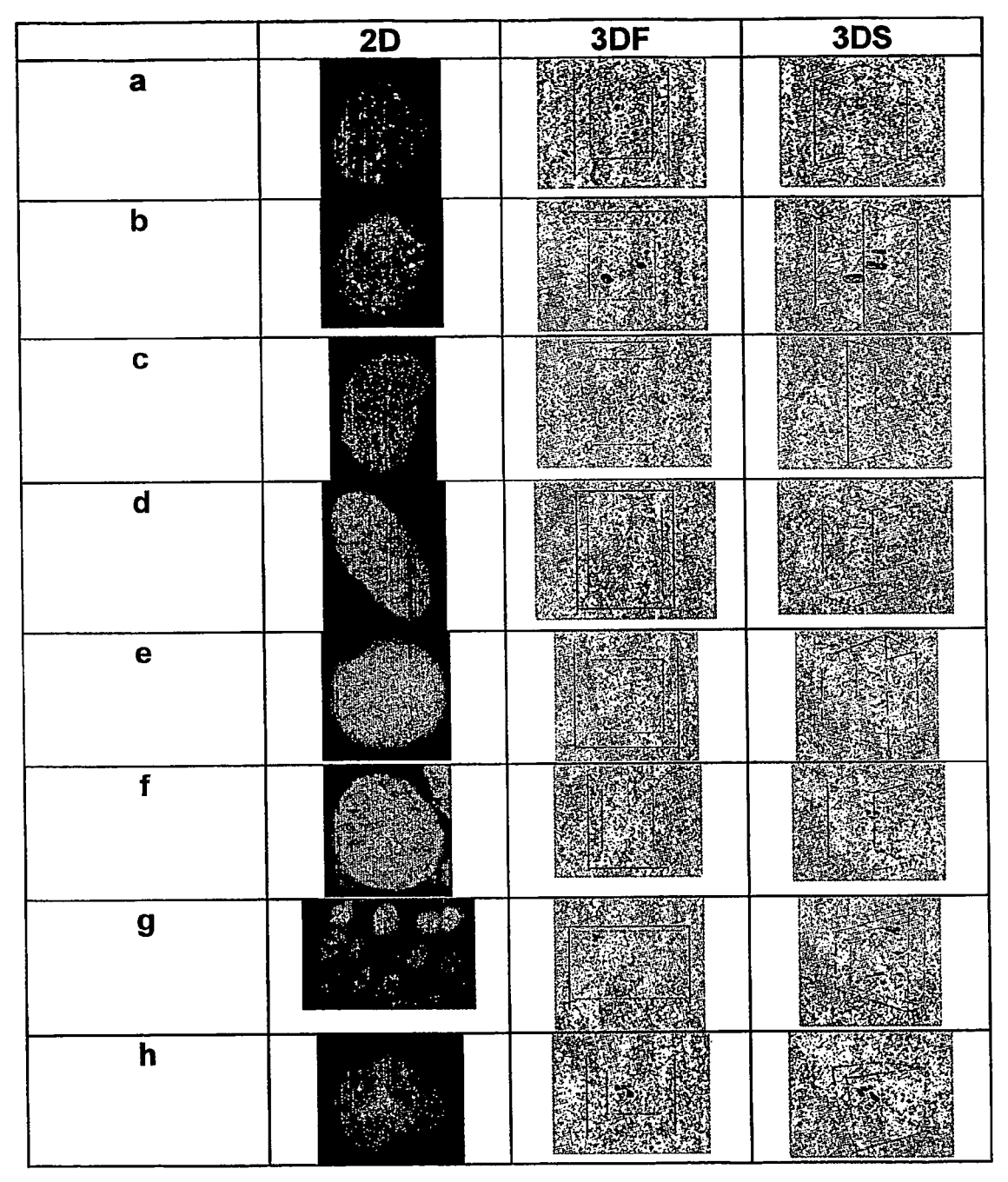

The question of whether or not this 3D organization was present in non-tumorigenic immortalized cells was addressed next. It was observed that the telomeric organization of normal cells is maintained in immortalized diploid cells as documented in the 3DS position that best illustrates the organization of the telomeres (FIG. 7*a*). However, there are consistent alterations of telomeric organization in immortalized tetraploid mouse and human cell lines (FIG. 7*b*, FIG. 10 and data not shown). Such tetraploid cells show a double telomeric disk, consisting of two individual TDs, with telomeres that synchronously decondense or condense in the 3D space of the nucleus.

Figure 7:
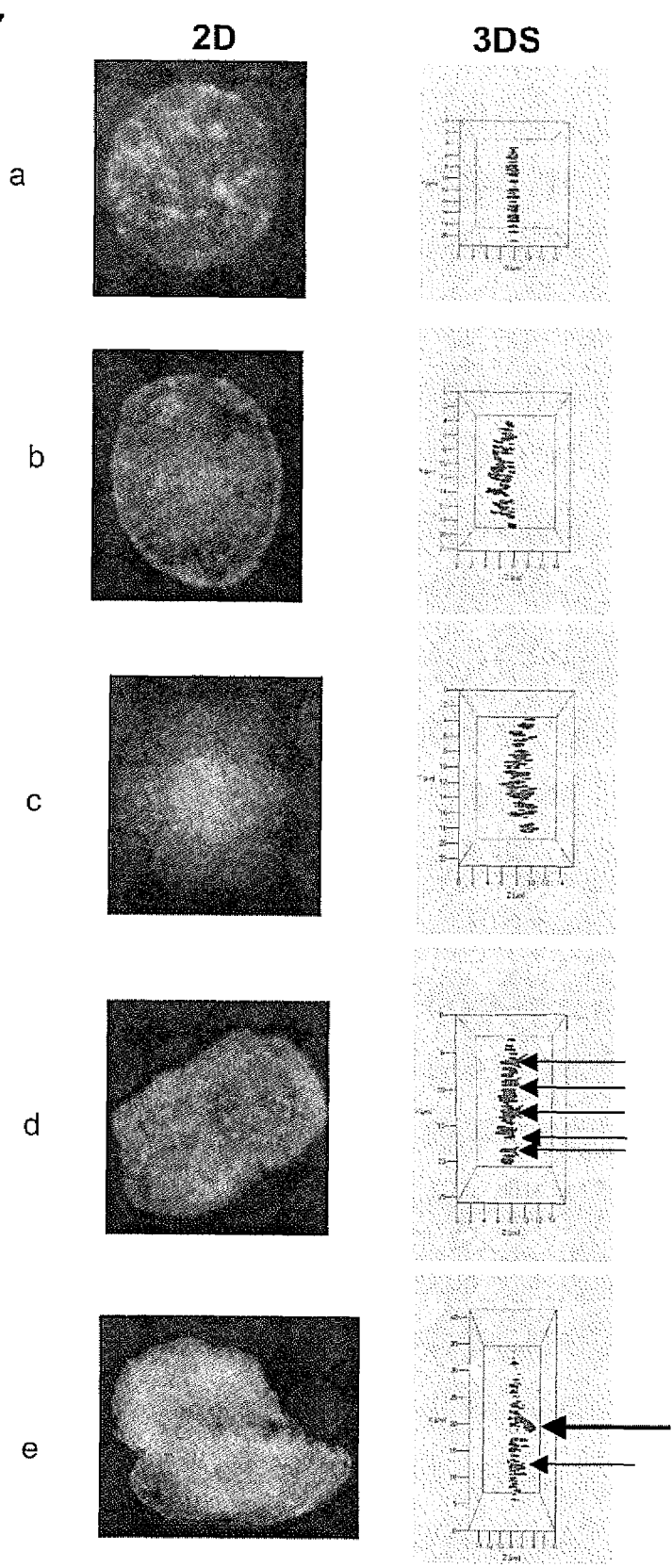
FIG. 7 illustrates telomere organization in interphase nuclei of immortalized and tumor mouse and human cell lines. To better illustrate the localization of telomeres, they are represented in the telomeric disk (TD) state (for details, see text). As indicated, the telomeres are shown in 2D and 3DS. Abbreviations as in FIG. 4A. *a* v-abl immortalized mouse Pre-B lymphocyte line[26]. b Spontaneously immortalized tetraploid mouse BAF3 cells[27]. c Telomere organization in spontaneously immortalized tetraploid HaCaT cells[25]. d Telomere organization in human tumor cell lines in Colon320DM[28] and e in SH-EP[29]. Telomere aggregations and distorted disks are indicated by arrows.
Figure 8:
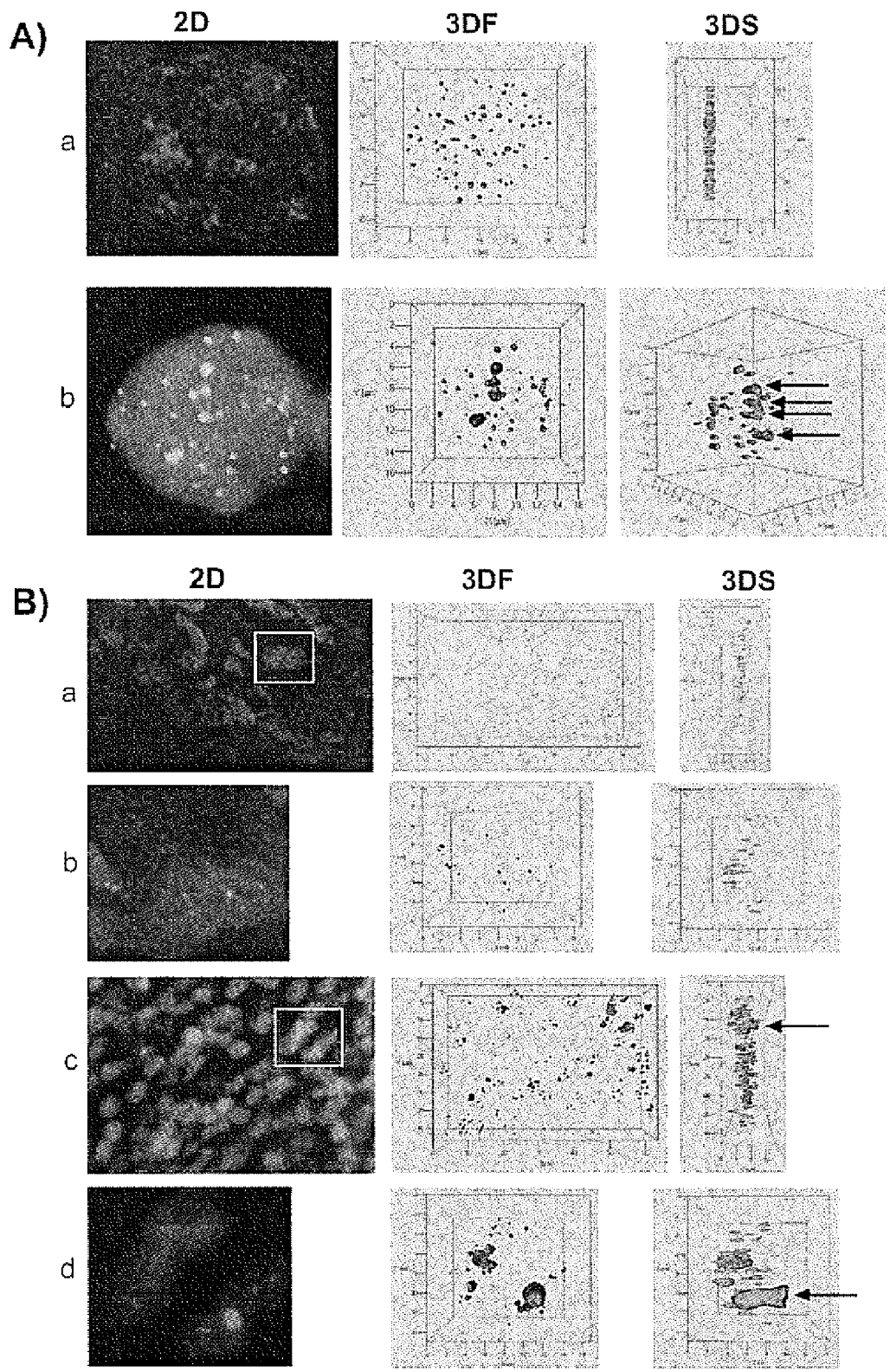
FIG. 8 illustrates telomere organization in interphase nuclei of mouse and human tumors. 8A. Telomere organization in mouse tumor and control cells. a Normal splenocytes and b mouse plasmacytoma DCPC21[30]. Telomeres are shown in 2D and 3D respectively for abbreviations, see FIG. 4A. Telomere aggregations and distorted disks are indicated by arrows. 8B. Telomere organization in human tumor and control tissues. Telomeres are shown in 2D and 3D for a Control epithelial tissue, overview and b insert images, and c head and neck squamous cell carcinoma tissue, overview and d insert images. Telomere aggregations and distorted disks are indicated by arrows.

In contrast to the above data, a new complex telomeric organization is found in tumour cell lines (FIGS. 7*c* and *d*, and FIG. 10). More importantly, this new telomeric organization is not a tissue culture artifact but intrinsic to tumor cells, as demonstrated in FIG. 8, panel b, and FIG. 8B, panels c and d, arrows. Colon carcinoma and neuroblastoma cell lines (FIGS. 7*c* and *d*, and FIG. 10) as well as primary mouse plasmacytoma and human head and neck squamous cell carcinoma (stage IV) (FIGS. 8A and B, and FIG. 10) show a similar reorganization of the 3D nuclear space. All tumor cells show large aggregates or aggregations of telomeres of various levels of complexity so that telomeres fail to properly align in the TD (FIGS. 7 and 8). This structural alteration coincides with the distortion of the TD (FIGS. 7 and 8). Moreover, aggregated or fused telomeres protrude outside of the TD space thus enlarging the TD space considerably (FIGS. 7 and 8, see inserts and arrows). In addition, it is striking that individual non-aggregated or fused telomeres are also not properly integrated into the TD (FIGS. 7 and 8). The new TD of tumor cells is enlarged unevenly by two to four folds, with size variations from tumor cell to tumor cell reflecting the polyclonal nature of ongoing genomic instability. In contrast, control mouse primary splenocytes and control human epithelial tissue, the latter taken 2 cm away from the primary tumor, reveal the regular and organized structure of the telomeres (FIG. 8A, panel a, and FIG. 8B, panels a and b, and FIG. 10). In conclusion, telomeres of tumor cells form an altered telomeric organization, occupying a 3D space that differs from their normal counterparts.

Figure 9:
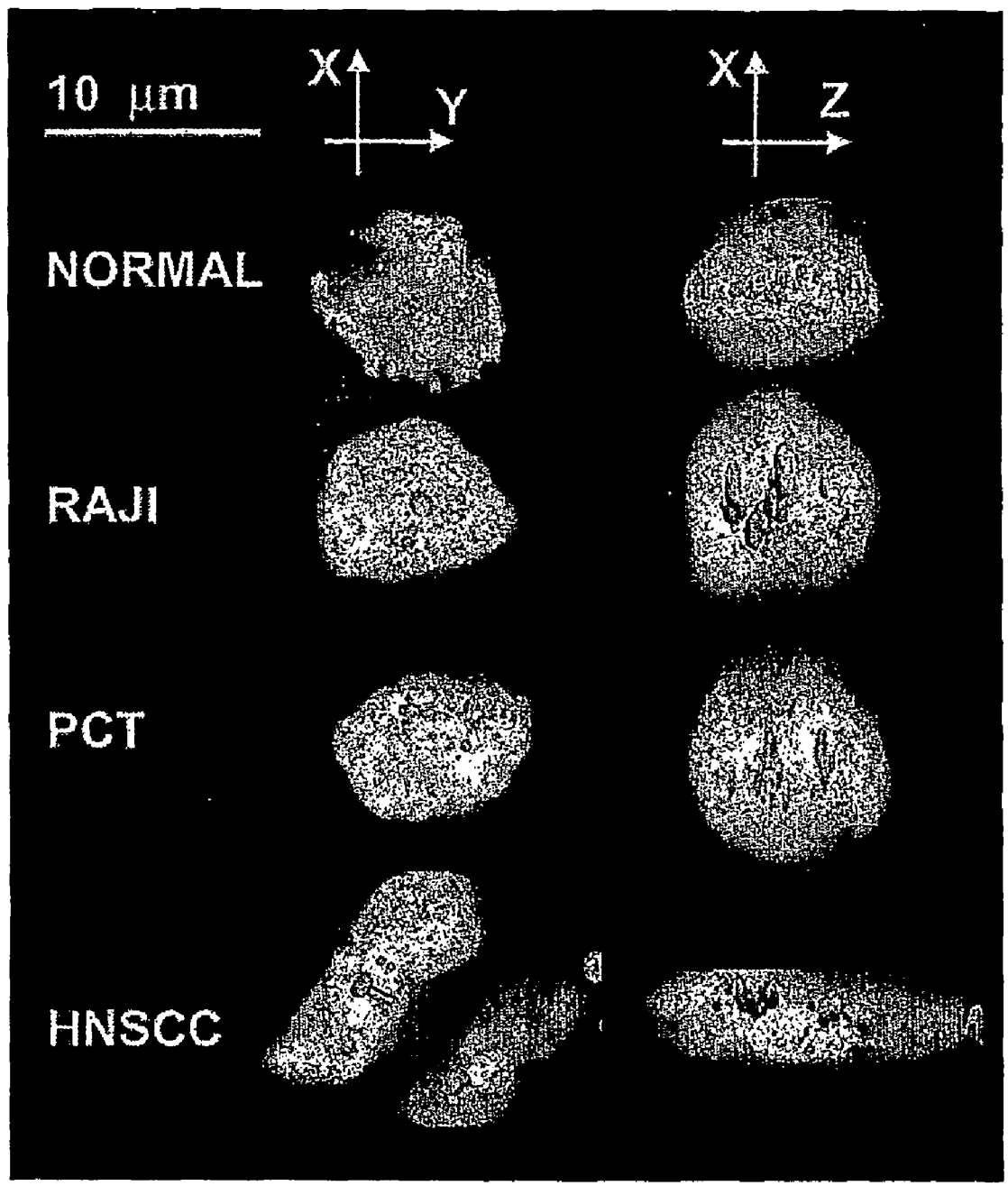
FIG. 9 illustrates the distribution of telomeres in interphase nuclei of cancer cells compared to a normal cell. Images are shown as explained in FIG. 5. Normal: A normal blood cell. RAJI: A Burkift lymphoma cell line. PCT: a primary mouse plasmacytoma cell. HNSCC: A primary human head and neck squamous cell carcinoma (stage IV). Aggregates of telomeres are formed and the telomere disk is distorted.

The distribution of telomeres in other cancer cells was observed. Typical images constructed from normal nuclei (FIGS. 9 and 10) and from a Burkitt lymphoma cell line (FIGS. 9 and 10, Raji) as well as from primary mouse plasmacytoma and primary human head and neck squamous cell carcinoma (stage IV) (FIGS. 9 and 10, PCT and HNSCC) show that telomeres form aggregates and thus a partially altered TD. Such telomere aggregates are characterized by both a larger volume and a larger integrated intensity than their normal non-overlapping and non-aggregated counterparts. They are not observed in normal cells. Similar results on altered telomeric organization were also found in human neuroblastoma and colon carcinoma tumor cell lines.

Tables 2 to 8 show the number of aggregates and the number of dividing telomeres in normal controls, immortalized cell lines, cancer cell lines and cancer samples.

Chromosomal Organization.

Figure 11:
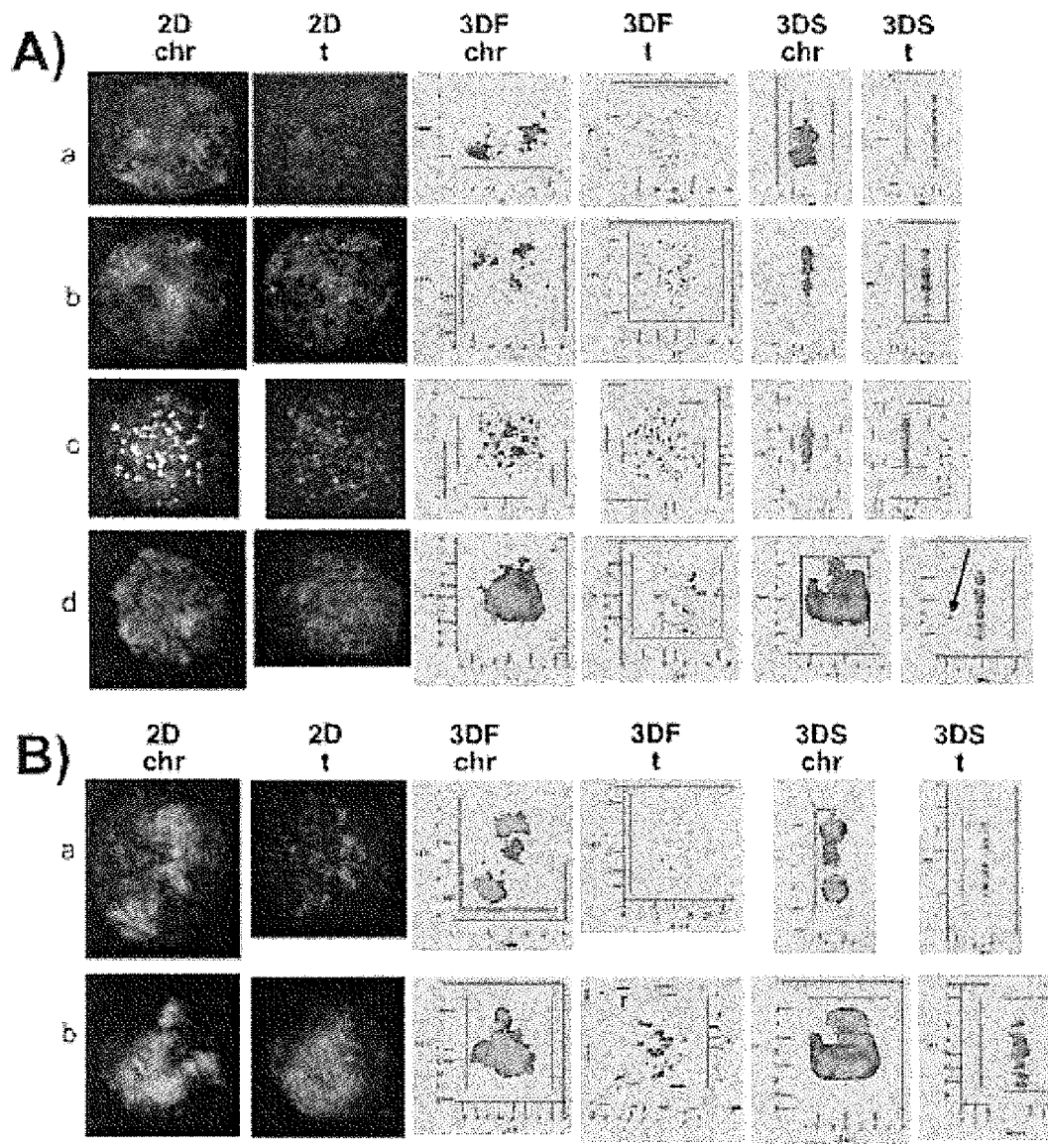
FIG. 11 illustrates telomere and chromosome organization in 3D mouse and human interphase nuclei of normal, immortalized and tumor cells. Abbreviations as in FIG. 4A. chr: chromosomes, t: telomeres. 11A. Telomere and chromosome organization in 3D mouse nuclei of normal, immortalized and tumor cells. Chromosome painting was carried out with chromosome 11 paint, and images were acquired and analyzed in 2D and 3D for primary spleen cells a, immortalized Pre-B cells with trisomy 11. b, and tumor cells (plasmacytoma DCPC21). c In addition, the whole genome was visualized following mouse SKY, showing the arrangement of all chromosomes in the 3D nuclear space. However, only Cy3 and FITC filters were available for deconvolution. d Shows the same analysis performed for the plasmacytoma DCPC21. Note the change in 3D space occupied by chromosome 11 in Pre-B cells trisomic for chromosome 11 and in mouse plasmacytoma and a dislocated telomere (3DSt). Telomere hybridization was performed for the identical cells and is shown for each of the images presented. 11B. Telomere and chromosome organization in 3D human nuclei of normal and tumor cells. Chromosome painting was carried out with chromosome 1 (green) and chromosome 21 (red), and images were acquired and analyzed in 2D and 3D for primary human lymphocytes a, and for the human colon carcinoma line Colo320DM b. Note that only 11 images were deconvolved for 11A and all images gave similar results. Arrows depict chromosomal rearrangements between chromosomes 1 and 21. Telomere hybridization was performed for the identical cells and is shown for each of the images presented. Telomere aggregations and distorted disks are indicated by arrows.

These data prompted us to examine whether telomeric aggregates or aggregations and distorted alignment of telomeres are associated with changes in chromosomal organization within the identical 3D nucleus. Consistent with the ordered localization of the telomeres in primary human and mouse cells, chromosomes display an ordered localization in the 3D nuclear space (FIG. 11A, panel a and FIG. 11B, panel a). Both mouse chromosomes 11 are consistently seen in two distinct territories in normal cells and properly aligned in the TD (FIG. 11A, panel a). Surprisingly, the TD is maintained in immortalized mouse B cells with trisomy 11 (FIG. 11A, panel b). Although the additional chromosome 11 occupies a distinct 3D intranuclear space that differs from the chromosome 11 organization in diploid cells (FIG. 11A, panel a), telomeres and chromosomes of these cells perfectly align along the TD (FIG. 11A, panel b). Thus, the 3D interphase nuclear space appears to tolerate an additional chromosome by aligning it along the TD. In fact, using mouse spectral karyotyping for the same cells, it was found that all chromosomes properly align along the TD (FIG. 11A, panel c). The 3D organization of chromosome 11 in mouse tumor cells was examined next. As illustrated in FIG. 11A (panel d), the order of chromosome 11 positioning is altered. The chromosomes 11 are dispersed widely throughout the 3D space of the nucleus (FIG. 11A, panel d, 3DF chromosomes (chr)). Concomitantly, chromosomes 11 are also improperly aligned along the TD (FIG. 11A, panel d, 3DS chr). Also, this TD shows some telomeric aggregations or aggregates, and one telomere is not integrated into the TD (FIG. 11A, panel d, 3DS telomeres (t) (arrow)).

Based on these findings, the 3D positioning of two chromosomes in the 3D intranuclear space was studied. The localization of chromosomes 1 (green) and 21 (red) in human primary and tumor cells was investigated (FIG. 11B). There is a clear spatial organization of chromosomes 1 and 21 in primary human cells. Both chromosomes occupy distinct territories and properly align along the telomeric disk (FIG. 11B, panel a, 3DF chr and 3DS chr). Significantly, as highlighted in human colon cancer cells, this order is altered in human tumor cells (FIG. 11B, panel b). Chromosomes 1 and 21 have left their distinct territories so that these two chromosomes are placed into illegitimate close proximity with each other. It was observed that their genetic material intermingles as evident by the mixed colour signatures of both chromosomes (FIG. 11B, panel b, 3DF chr and 3DS chr). Thus, it appears that tumor cells can easily reorganize their genomes through the exchange of genetic material as their telomeres aggregate and chromosomes alter their 3D positions. This is the first time that chromosomal and telomeric rearrangements can be structurally linked to each other in the 3D compartment of the nucleus.

Example 2 c-Myc Deregulations Alters 3D Organization of Telomeres and Chromosomes of the Interphase Nucleus.

Methods

Cells

Cell lines, culture conditions and c-Myc induction for Pre-B and BAF3 cells have been described elsewhere (BAF3[27], Pre-B[28]). The primary plasmacytoma DCPC21 was isolated from a BALB/c mouse[30]. v-abllmyc-induced plasmacytomas were collected from BALB/c mice. MycER was activated as described previously[27,28].

Telomere FISH.

BAF3, Pre-B and plasmacytoma cells were fixed in suspension with 3.7% formaldehyde (3D fixation). Telomere FISH was performed as described[32] using a Cy3 labeled PNA telomere probe (DAKO, Glostrup, Denmark). Telomere hybridizations were specific as shown by metaphase hybridizations and the correct number of the telomeric signals observed at the ends of chromosomes prepared from primary cells.

Chromosome Painting.

Chromosome painting was carried out according to standard protocols[31] using a mouse chromosome 11 (Cy3) and 15 (FITC) paints from CedarLane (Hornby, ON, Canada).

Spectral Karyotyping (SKY).

Mouse spectral karyotyping (SKY) was carried out as described[30]. SKY was performed over a 10 day period. Significant values for chromosomal rearrangements per individual chromosome are indicated with Myc activation as well as without Myc activation. Mean total chromosomes, as well as numbers of each specific chromosomes observed for control and Myc-activated cells were compared over time by two-way analysis of variance. For other chromosomal aberrations, such as aggregations, translocations and deletions, common (at least 10%) incidences in specific chromosomes were also compared for both groups of cells over time with the Mantel-Haenzsel stratified analysis.

3D Image Acquisition.

A minimum of 20 and a maximum of 30 nuclei were analyzed by 3D imaging using Axioplan 2 (Zeiss) with 100 W fluorescence, a cooled AxioCam HR B&W with 1× adaptor (Zeiss). DAPI, FITC and Cy3 filters (Zeiss) were used in combination with Planapo 63×/1.4 oil (Zeiss). Axiovision 3.1 software with deconvolution module and rendering module were used (Zeiss). 80-100 sections were acquired for each fluorochrome at 100 and 200 nm respectively. The constrained iterative algorithm option was employed[33] and surfaces rendered in x, z and x, y axes.

3D Analysis of Telomeres.

To define telomere parameters and the distribution of telomeres inside the volume of the nucleus, a special 3D image analysis program was developed. The program segments the nucleus, counts the telomeres and analyzes the size shape and intensity of each one. Finally, the distribution of telomeres inside the nucleus was analyzed. It compared the volume of the nucleus itself (as calculated from the 3D DAPI image) with the volume and the shape of the volume that was occupied by the telomeres.

Results

Distinct and Non-Overlapping Telomere Territories in Normal and Immortalized, Nontumorigenic B Cells.

In the present study, the inventors examined whether the deregulation of the oncogene c-Myc affected the 3D organization of telomeres in the interphase nucleus. To this end, the effect of a transient activation of c-Myc was examined using two independent immortalized cell lines BAF3[37] and Pre-B[28] stably transfected with MycER[TM35] . In addition, a mouse model of c-Myc-dependent tumorigenesis, the mouse plasmacytoma (PCT)[36] was studied. The first step of this study was the analysis of the 3D nuclear organization of telomeres in the non-MycER-activated BAF3 and Pre-B cells as well as in primary BALB/c B lymphocytes that served as a control for all BALB/c mouse PCTs.

Figure 12:
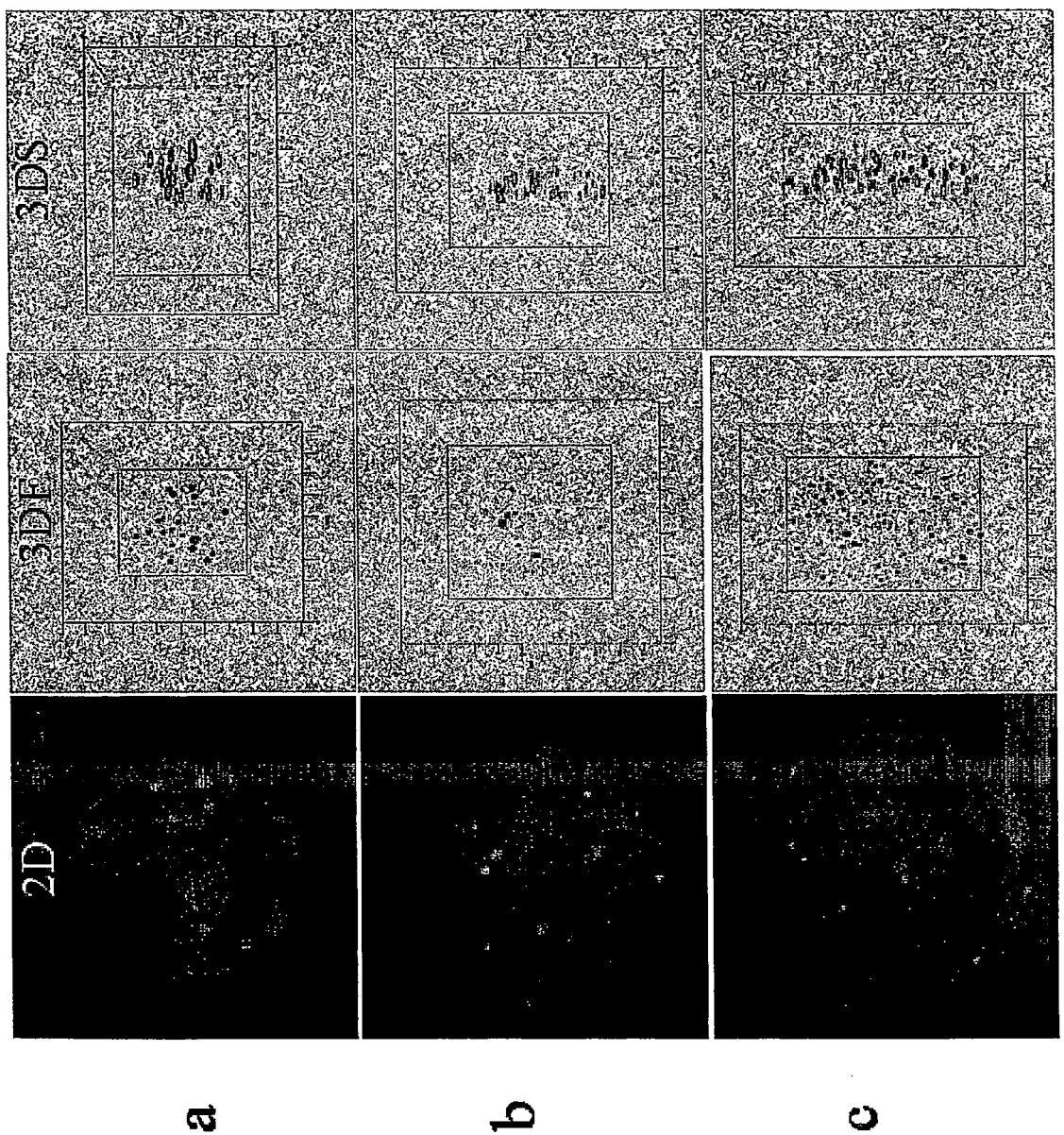
FIG. 12 illustrates telomeric organization in two-dimensional and three-dimensional interphase nuclei of primary and immortalized mouse B-lymphocytes. a: Primary BALB/c lymphocyte nucleus in G0/G1 phase of the cell cycle. The a/c ratio is 1. b: Nucleus of Pre-B mouse lymphocyte, immortalized, non-tumorigenic in G1/S phase telomeric organization. The a/c ratio is 8.8. c: Baf3 mouse pro B lymphocyte in G1-S phase telomeric organization, immortalized, non-tumorigenic. The a/c ratio is :5.5. 2D: two-dimensional analysis of telomeres in the interphase nucleus. 3DF: three-dimensional analysis of the telomeres in the interphase nucleus, front view. 3DS: three-dimensional analysis of the telomeres in the interphase nucleus, side view. Telomere hybridizations and imaging in 2D and 3D were as outlined herein.

Telomeres of primary BALB/c B cells showed non-overlapping telomere territories (TTs) as determined by 3D imaging and mathematical analysis (FIG. 12, panel a). In the absence of MycERTM activation, both Pre-B and BAF3 interphase nuclei also displayed distinct and non-overlapping TTs (FIG. 12, panels b and c) non distinguishable from TTs of the primary mouse B cell nuclei. This allowed the study of the effects of regulatable Myc activation on the 3D telomeric organization.

c-Myc-Dependent Disruption of the 3D Nuclear Organization of Telomere Territories.

To test c-Myc's potential impact on the 3D nuclear telomeric organization, the effect of a transient activation of c-Myc on the 3D telomeric organization of BAF3 and Pre-B interphase nuclei was analyzed. After a transient activation of MycER with 4-hydroxy-tamoxifen (4HT), both cell lines exhibited alterations in their telomeric organization forming telomeric aggregates (Tables 9 and 10, FIGS. 13 and 14). Telomeric aggregates appear as early as 24 hours after c-Myc activation. The number of telomeric aggregations peaked at 72 hours with highest statistical significance (p=0.0012; Tables 9 and 10, FIGS. 13 and 14).

c-Myc Transiently Remodels the 3D Nuclear Organization of Telomeres.

Figure 13:
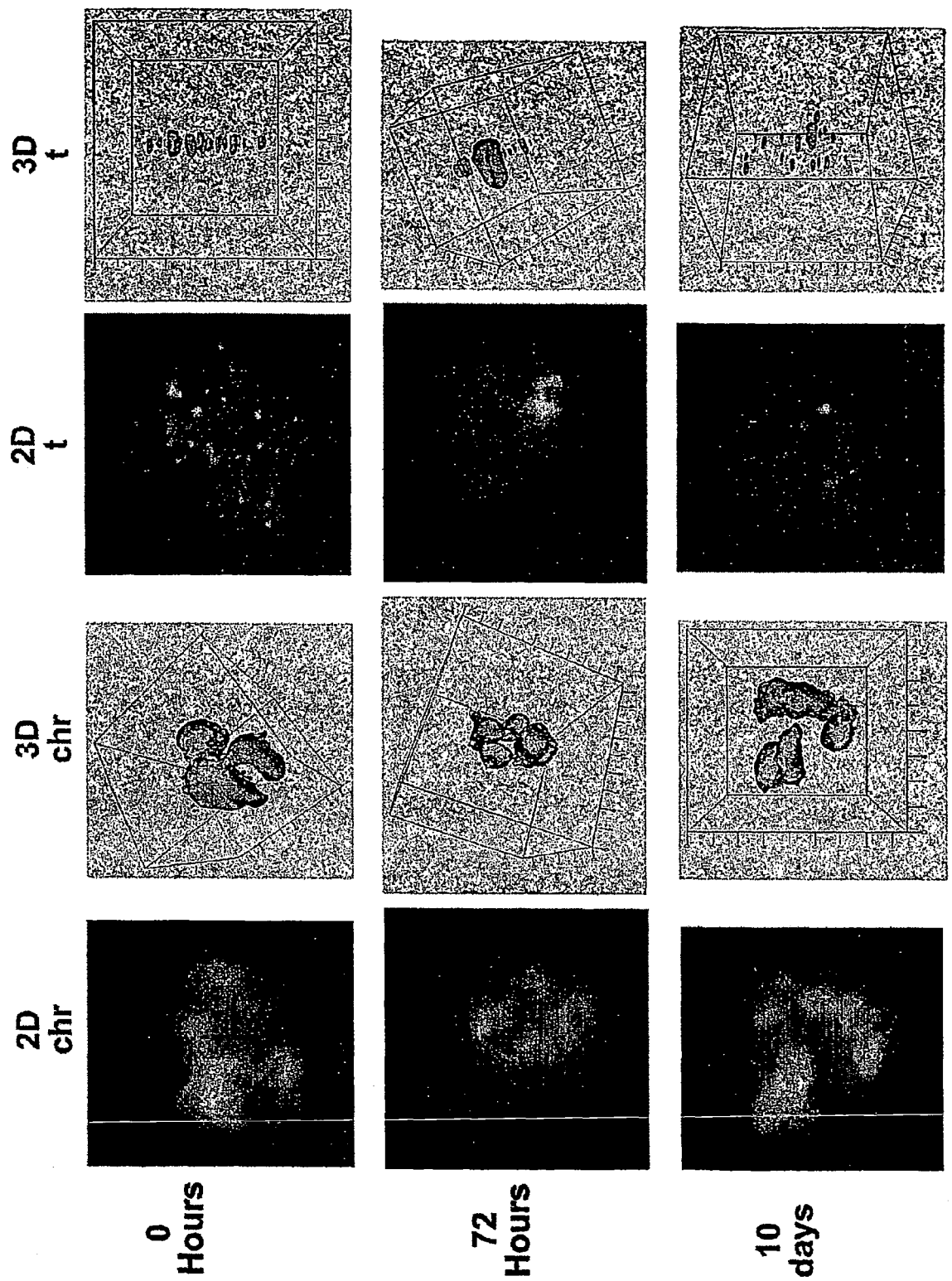
FIG. 13 illustrates telomere and chromosome organization in interphase nuclei of MycER-activated mouse B-lymphocytes (Pre-B). The identical nuclei have been probed for chromosomes and telomeres. Left panels show the two-dimensional (2D) images of FISH with chromosome paints at 0 hours, 72 hours, and 10 days. Blue: DAPI, red: chromosome 11, green: chromosome 15. Second panel to the left shows the same image after three-dimensional (3D) analysis. The DAPI channel has been inactivated in order to visualize the red (chromosome 11) and green (chromosome 15) signals within the nucleus. Note the mixed color signatures of chromosomes 11 and 15 at 72 hours. The two subsequent panels to the right show telomere hybridizations in 2D and 3D respectively. 2D t: shows the telomeric signals (red) seen in 2D nuclei at 0 hours, 72 hours and 10 days. 3D t: shows the telomeric signals (red) seen in 3D nuclei at 0 hours, 72 hours and 10 days. Note the telomere aggregates at 72 hours. Similar results were obtained with BAF3 cells. 2D chr: two-dimensional image of chromosomes; 3D chr: three-dimensional image of chromosomes. 2D t: two-dimensional image of telomeres; 3D t: three-dimensional image of telomeres.
Figure 14:
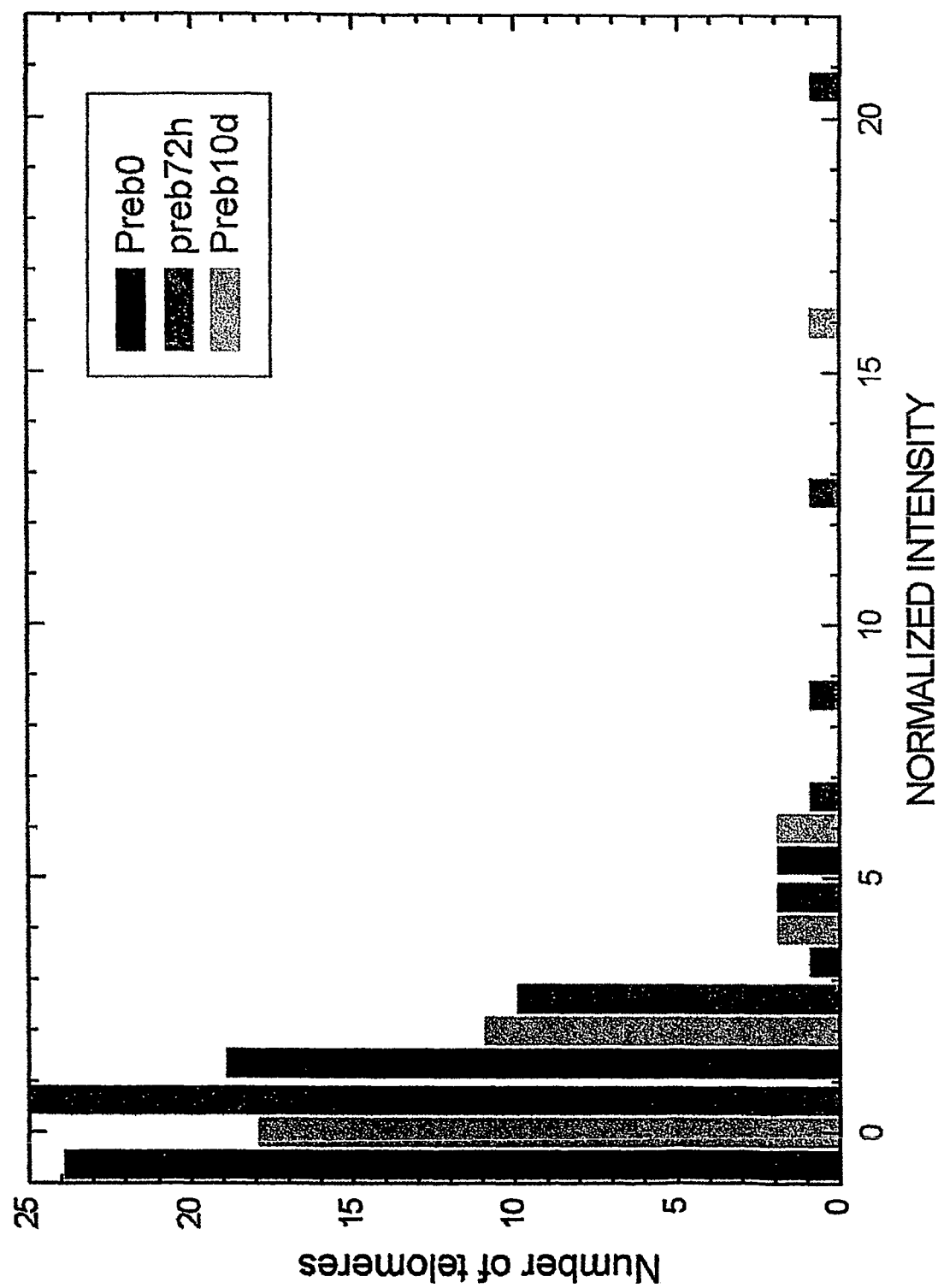
FIG. 14 illustrates telomere organization in interphase nuclei of MycER-activated mouse B-lymphocytes (Pre-B). Measurement of telomeric signals in the interphase nuclei of MycER-activated mouse B-lymphocytes (Pre-B) shown in FIG. 13. Note the increase in normalized intensity at 72 hours after c-Myc deregulation. This corresponds to the formation of telomeric aggregates. This peak in aggregate formation (see also Table 9) is reversible after c-Myc deregulation ceases. At 10 days, the telomeric order is almost identical to the one measured for 0 hours. 0 hours: black, 72 hours: dark grey, 10 days: grey. The measurements were carried out with a novel software that was developed by the present inventors.
Figure 15:
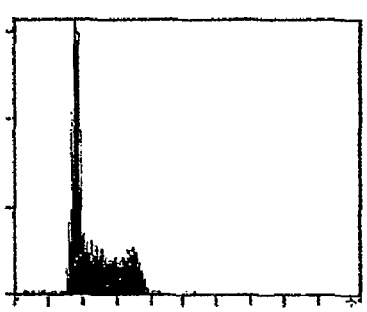
FIG. 15 illustrates FACS analysis of MycER-activated mouse pro B lymphocytes (BAF3). Cells were analyzed by FACS and the viability of the culture was assessed at 0, 1, 3-10 days. The sub-G1 cells in cultures grown in the absence or presence of 4HT was identical.
Figure 15:
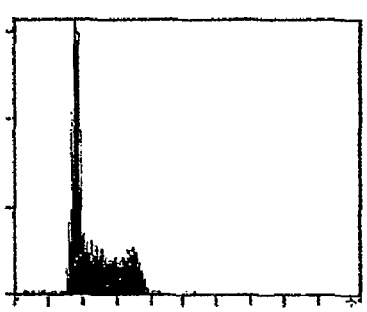
Figure 15:
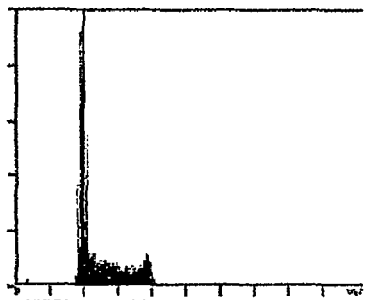
Figure 15:
Figure 15:
Figure 15:
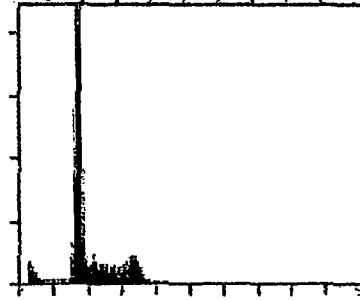
Figure 15:
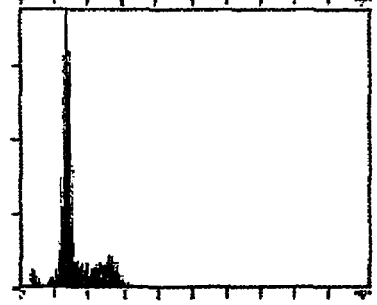

After the effects of a transient c-Myc deregulation subsided, within a period of 6 to 10 days, the re-organization of the TTs towards their apparently normal 3D telomeric configuration that did not show any overlapping TTs and no telomeric aggregates was observed (Tables 9 and 10, FIG. 13, panel c, 3D t). FIG. 14 summarizes these findings graphically. These data indicate that the telomeres can alter their organization and form aggregates transiently and in a c-Myc-dependent fashion. Importantly, the reversal of the telomeric order to an almost original state was not due to growth arrest or cell death as confirmed by flow cytometry (FIG. 15). It therefore seems that withdrawal of c-Myc deregulation allows for a re-establishment of a 3D telomeric organization without aggregated TTs. It is concluded that c-Myc deregulation can transiently trigger the aberrant organization of the 3D telomeric space.

c-Myc-Dependent Disruption of the 3D Nuclear Organization of Chromosome Territories (CTs).

Because the data demonstrated that c-Myc deregulation remodels the 3D intranuclear telomeric organization, the organization of CTs was then examined. The inventors analyzed whether c-Myc-dependent formation of shared TTs was associated with changes in chromosomal organization within 3D nuclei. To this end, MycER-activated Pre-B cells were hybridized with two chromosome paints for chromosome 11 (red) and 15 (green) mostly involved in c-Myc-dependent oncogenesis of B lineage cells[36,37].

The 3D organization of chromosomes and telomeres was studied over a time course of 10 days, in a c-Myc-dependent manner (FIGS. 13 and 14). At 0 hour, chromosomes 11 and 15 were found in their respective non-overlapping CTs (FIG. 13, panel a, 3D chr (chromosomes)). Similarly, the telomeres of immortalized cells did not show overlaps or aggregations (FIG. 13, panel a, 3D t). At 72 hours following Myc deregulation, chromosomes 11 and 15 were observed in altered territories in which they shared overlapping illegitimate territories as documented by the mixed color signatures representing these two chromosomes (FIG. 13, panel b, 3D chr). As illustrated in a representative example, the identical 3D nucleus displayed telomeric aggregations within the same 3D space that encompasses chromosomes 11 and 15 in altered territories (FIG. 13, panel b, 3D t). At day 10, both chromosomes 11 and 15 and the telomeric organizations assumed 3D nuclear spaces devoid of shared CTs and TTs (FIG. 13, panel c). Thus, a transient deregulation of c-Myc leads to reversible remodeling of both CTs and TTs.

Spectral Karyotyping Confirms Chromosomal Rearrangements and Remodulation of 3D Interphase Nucleus.

A survey of chromosomal rearrangements in MycERTM-activated BAF3 and Pre-B cells over a 10 day period was then examined. MycER was activated by 4HT[30] for a single time, and cells were harvested at 0, 24, 48, 72 hours, and 10 days. Using spectral karyotyping (SKY) that allows the simultaneous visualization of all chromosomes in one metaphase, an increase in chromosomal aberrations for 72 hours, and a decrease for 10 days were found. For example, 60% of the metaphases showed clear structural and numerical chromosomal aberrations at 72 hours, and these numbers decreased to 43% at 10 days, as calculated from 20 metaphases per time point. As to chromosome 15, it was non-randomly rearranged over time and as a function of c-Myc deregulation (ρ=0.001, Table 11). Numerical changes were also observed for this chromosome. Numerical and structural aberrations of chromosome 11 occurred but were not statistically significant (Table 11). From the above SKY data, it was shown that both 3D interphase and 2D SKY data follow a similar trend: both sets of experiments complement each other and confirm that c-Myc deregulation induces chromosomal rearrangements. Moreover, the 3D nuclear alterations of telomere and chromosome positions observed here for the first time as a result of c-Myc deregulation reflect chromosomal instability as documented by SKY.

Aberrant 3D Telomeric and Chromosomal Organization in Primary Plasmacytomas.

Using primary mouse tumors with c-Myc overexpression, the occurrence of c-Myc-dependent aberrations of the 3D nuclear organization of TTs and CTs in vivo was then examined. The mouse plasmacytoma (PCT) in which c-Myc is constitutively activated through chromosomal or extrachromosomal translocation to one of the immunoglobulin loci was the in vivo model used[36,30]. PCTs induced by viral myc do not carry these translocations because myc is already constitutively activated due to virally-driven myc overexpression[37].

Figure 16:
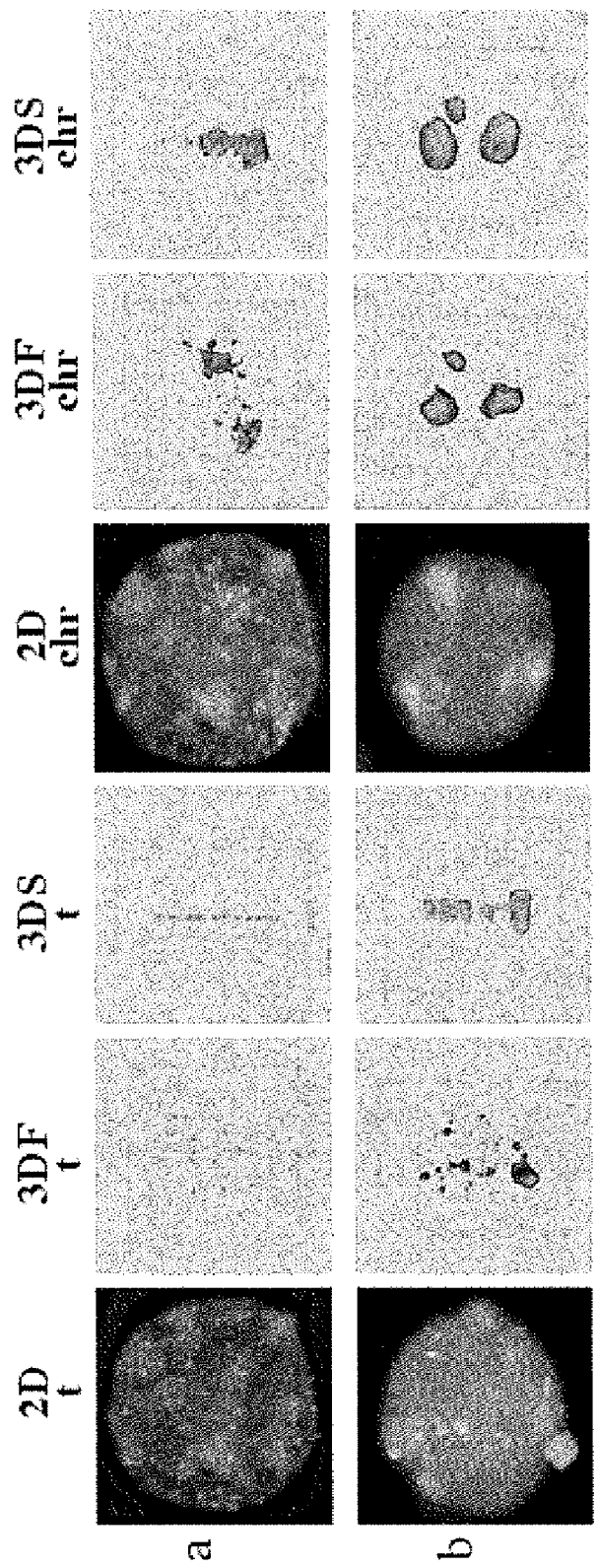
FIG. 16 illustrates the organization of chromosomes and telomeres in primary mouse plasmacytoma. 2D and 3D images show the organization of telomeres (t) and of chromosome 11 (chr) in interphase nuclei (blue) of primary mouse plasmacytoma and control primary B cells. Panel a: primary mouse B cells, panel b: primary mouse plasmacytoma cells. The abbreviations are as given in FIG. 13.

Primary BALB/c PCTs were analyzed by 3D imaging, and the telomeric organization of PCT interphase nuclei were examined. Primary BALB/c lymphocytes served as control (FIG. 12, panel a, FIG. 16, panel a). The 3D intranuclear space of PCT nuclei exhibited an aberrant telomeric order, where telomeres formed aggregations and thus partially altered TDs (FIG. 16, panel b, arrows). This showed that an aberrant 3D nuclear organization of telomeres is consistently observed in primary PCTs but is absent in normal B cells.

To examine potential 3D alterations in CTs of the same primary PCTs, mouse chromosome 11 was chosen, since it constitutes the most frequent chromosomal aberration in v-abl/myc-induced PCTs[37]. When compared to the organization of chromosome 11 territories in normal BALB/c lymphocytes, the 3D organization of chromosomes 11 in primary mouse PCTs[36,37] was disrupted (FIGS. 16 a and b). As illustrated in FIG. 16, panel b, a representative PCT with trisomy 11 showed altered positioning of one chromosome 11 as well as telomeric aggregations. In contrast, chromosomes 11 displayed an ordered localization in the 3D nuclear space of primary B cells (FIG. 16).

These data confirm alterations in CTs and TTs when c-Myc is deregulated in primary tumors. For the first time chromosomal and telomeric rearrangements are structurally linked to each other in the 3D compartment of the nucleus, in a c-Myc-dependent manner.

Example 3

Biological Dosimetry

Figure 17:
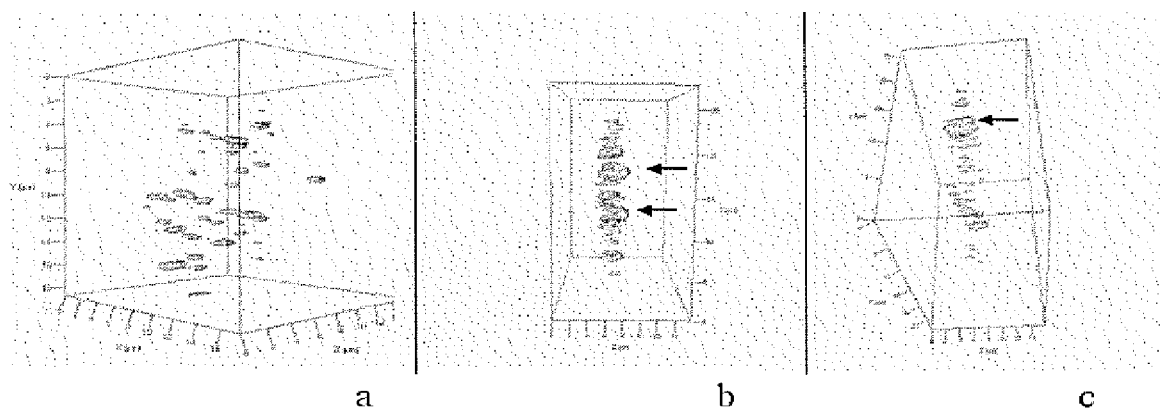
FIG. 17 illustrates that 3D telomeric organization in interphase nuclei are altered as a result of radiation exposure. a: 3D telomeric organization in lymphocyte line without radiation exposure. b and c: 3D telomeric organization after 12 and 24 hours of radiation exposure (6Gy) respectively.

Biological dosimetry is based on investigations of induced biological effects (biomarkers) that are correlated with radiation dose. In particular, scoring of induced chromosomal aberration from peripheral lymphocytes has been developed into a valuable dosimetric tool in radiological protection. Biomarkers can be defined as biological endpoints (such as cellular and molecular changes) used to indicate an exposure to ionizing radiation (IR), representing an early event that occurs as a result of IR interaction with living tissues. The inventors have shown that gamma-irradiation alters the 3D organization of telomeres within short periods of time (12 hours) (FIG. 17).

Example 4

Telomeric Organization in Breast Cancer Tissue

Figure 18:
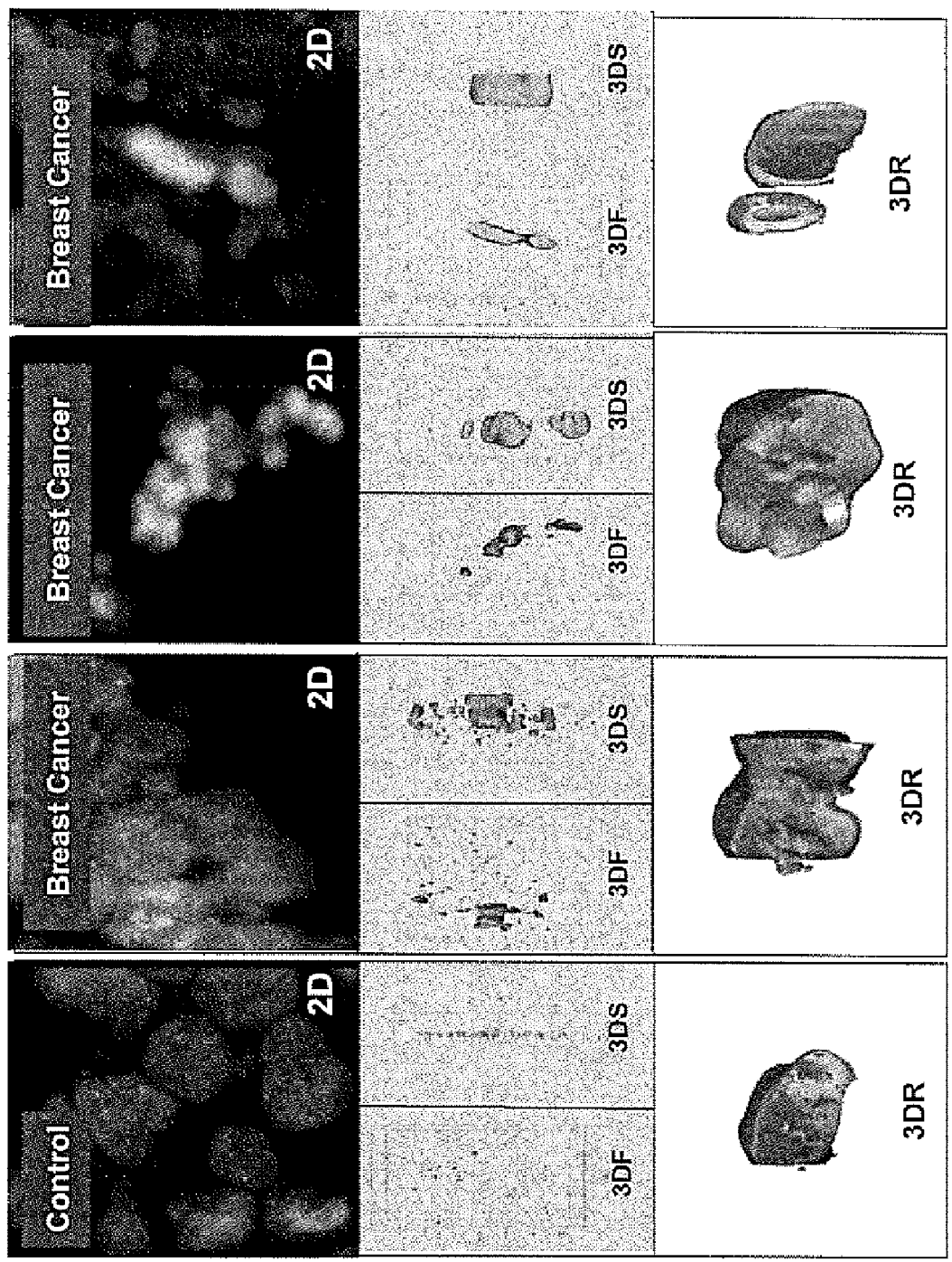
FIG. 18 illustrates two-dimensional and three-dimensional images of interphase nuclei of control mammary tissue and breast cancer. 3D reconstructions for each of the patients are shown in bottom panels (3DR). (see also Table 8). Note that there are no telomere aggregations in normal breast tissue. Telomeres are shown in red. Nuclei are shown in blue. The 3D images show telomeres only. 3DF: three-dimensional front view; 3DS: three-dimensional side view. 3DR: 3D reconstruction by YG. Magnification of 2D images: 63×/1.4 oil Planapo (Zeiss). 3D images were rendered as described (Chuang et al, 2004).

Telomeric aggregations were compared in six age- and grade-matched breast cancer patients, all were grade 3. FIG. 18 is a representative results for the breast cancer patients. FIG. 18 and Table 8 shows there is a significant difference in 3D telomeric volumes and telomeric aggregations between breast cancer cells and controls.

In further experiments, it has also been shown that the absence of genome repair coincides with alterations in the disk. The above studies show that:

- stresses on the cell which potentially result in malignancy also result in telomere aggregations;
- deregulation of a single oncogene may lead to initiation of malignancy and also leads to telomere aggregations;
- telomere aggregations present in preneoplastic lesions (mouse plasmacytoma, day 14 and 19); and found in early neoplastic cervical lesions;
- telomere aggregations represent genomic instability at a very early stage; and
- the c-myc mouse plasmacytoma study shows that telomere and chromosomal aberrations also occur in vivo.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR REFERENCES REFERRED TO IN THE SPECIFICATION

1. Hackett J A and Greider C W. Balancing instability: dual roles for telomerase and telomere dysfunction in tumorigenesis. *Oncogene* 21, 619-26 (2002).
2. Harrington L and Robinson M O. Telomere dysfunction: multiple paths to the same end. *Oncogene* 21, 592-7 (2002).
3. Maser R S and DePinho R A. Connecting chromosomes, crisis, and cancer. *Science* 297, 565-569 (2002).
4. Cremer T, Cremer C, Baumann H, Luedtke E K, Sperling K, Teuber V, Zorn C. Rabl's model of the interphase chromosome arrangement tested in Chinese hamster cells by premature chromosome condensation and laser-UV-microbeam experiments. *Hum Genet.* 60, 46-56 (1982). 5. Zalensky A O, Allen M J, Kobayashi A, Zalenskaya I A, Balhorn R, Bradbury E M. Well-defined genome architecture in the human sperm nucleus. *Chromosoma* 103, 577-90 (1995).
6. Vourc'h C, Taruscio D, Boyle A L, Ward D C. Cell cycle-dependent distribution of telomeres, centromeres and chromosome-specific subsatellite domains in the interphase nucleus of mouse lymphocytes. *Exp Cell Res* 205, 142-151 (1993).
7. Cerda M C, Berrios S, Fernandez-Donoso R, Garagna S, Redi C. Organisation of complex nuclear domains in somatic mouse cells. *Biology of the Cell* 91, 55-65 (1999).
8. Armstrong S J, Franklin F C H, Jones G H. Nucleolus-associated telomere clustering and pairing precede meiotic chromosome synapsis in *Arabidopsis thaliana*. *J Cell Science* 114, 4207-4217 (2001).
9. Rabl C. Über Zellteilung. *Morphologisches Jahrbuch* Gegenbaur C (ed) 10, 214-330 (1885).
10. Tanabe H, Muller S, Neusser M, von Hase J, Calcagno E, Cremer M, Solovei I, Cremer C, Cremer T. Evolutionary conservation of chromosome territory arrangements in cell nuclei from higher primates. *Proc Natl Acad Sci U S A* 99, 4424-9 (2002).
11. Cremer M, von Hase J, Volm T, Brero A, Kreth G, Walter J, Fischer C, Solovei I, Cremer C, Cremer T. Non-random radial higher-order chromatin arrangements in nuclei of diploid human cells. *Chromosome Res.* 9, 541-67 (2001).
12. Popp S, Scholl H P, Loos P, Jauch A, Stelzer E, Cremer C, Cremer T. Distribution of chromosome 18 and X centric heterochromatin in the interphase nucleus of cultured human cells. *Exp Cell Res.* 189, 1-12 (1990).
13. Ferguson M and Ward D C. Cell cycle dependent chromosomal movement in pre-mitotic human T-lymphocyte nuclei. *Chromosoma* 101, 557-565 (1992).
14. Holley W R, Mian I S, Park S J, Rydberg B. Chatterjee A. A Model for Interphase Chromosomes and Evaluation of Radiation-induced Aberrations. *Radiat Res.* 158, 568-580 (2002).
15. Parada L A and Misteli T. Chromosome positioning in the interphase nucleus. *Trends in Cell Biology* 12, 425-432 (2002).

16. Haberma F A, Cremer M, Kreth W J, von Hase J, Bauer K, Wienberg J, Cremer C, Cremer T, Solovei I. Arrangements of macro- and microchromosomes in chicken cells. *Chromosome Res* 9, 569-84 (2001).
17. Haaf T and Ward D C. Rabl orientation of CENP-B box sequences in Tupaia belangeri fibroblasts. *Cytogenet Cell Genet* 70, 258-62 (1995).
18. Hozak P, Jackson D A, Cook P R. Replication factories and nuclear bodies: the ultrastructural characterization of replication sites during the cell cycle. *J Cell Science* 107, 2191-2202 (1994).
19. Jackson D A and Cook P R. Replication occurs at a nucleoskeleton. *The EMBO J* 5, 1403-1410 (1986).
20. Getzenberg R H, Pienta K J, Ward W S, Coffey D S. Nuclear structure and the three-dimensional organization of DNA. *J Cell Biochem.* 47, 289-99 (1991).
21. Bradbury E M. Reversible histone modifications and the chromosome cell cycle. *Bioessays* 14, 9-16 (1992).
22. Artandi S E, Chang S, Lee S-L, Alson S, Gootlieb G, Chin L, DePinho R A.
Telomere dysfunction promotes non-reciprocal translocations and epithelial cancers in mice. *Nature* 406, 641-645 (2000).
23. O'Hagan R C, Chang S, Maser R S, Mohan R. Artandi S E, Chin L, DePinho R A. Telomere dysfunction provokes regional amplification and deletion in cancer genomes. *Cancer Cell* 2, 149-155 (2002).
24. Pienta K J, Partin A W, Coffey D S. Cancer as a disease of DNA organization and dynamic cell structure. *Cancer Res.* 49, 2525-2532 (1989).
25. Boukamp P, Petrussevska R T, Breitkreutz D, Hornung J, Markham A, Fusenig N E. Normal keratinization in a spontaneously immortalized aneuploid human keratinocyte cell line. *J Cell Biol.* 106, 761-71 (1988).
26. Mai S, Hanley-Hyde J, Rainey G J, Kuschak T I, Paul J T, Littlewood T D, Mischak H, Stevens L M, Henderson D W, Mushinski J F. Chromosomal and extrachromosomal instability of the cyclin D2 gene is induced by Myc overexpression. *Neoplasia* 1, 241-52 (1999).
27. Fest T, Mougey V, Dalstein V, Hagerty M, Milette D, Silva S, Mai S. c-MYC overexpression in Ba/F3 cells simultaneously elicits genomic instability and apoptosis. *Oncogene* 21, 2981-90 (2002).
28. Mai S, Hanley-Hyde J, Fluri M. c-Myc overexpression associated DHFR gene amplification in hamster, rat, mouse and human cell lines. *Oncogene* 12, 277-88 (1996).
29. Baker D L, Reddy U R, Pleasure D, Thorpe C L, Evans A E, Cohen P S, Ross A H. Analysis of nerve growth factor receptor expression in human neuroblastoma and neuroepithelioma cell lines. *Cancer Res.* 49, 4142-6 (1989).
30. Wiener F, Kuschak T I, Ohno S, Mai S. Deregulated expression of c-Myc in a translocation-negative plasmacytoma on extrachromosomal elements that carry IgH myc genes. *Proc Natl Acad Sci U S A* 96, 13967-72 (1999).
31. Beatty B, Mai S, Squire J. (Eds) FISH: A practical Approach. Oxford University Press (2002).
32. Figueroa R, Lindenmaier H, Hergenhahn M, Nielsen K V, Boukamp P.
Telomere erosion varies during in vitro aging of normal human fibroblasts from young and adult donors. *Cancer Res.* 60, 2770-4 (2000).
33. Schaeffer L H, Schuster D, Herz H. Generalized approach for accelerated maximum likelihood based image restoration applied to three-dimensional fluorescence microscopy. *J. Microscopy* 204, 99-107. 2001.
34. Tietze, H. Famous problems of mathematics: solved and unsolved mathematics problems from antiquity to modern times. New York:
Graylock Press, pp.28 and 40-41 (1965).
35. Littlewood, TD et al. (1995) *Nucleic Acids Res.* 23, 1686-90.
36. Potter, M. et al. (1992) *Carcinogenesis* 13, 1681-97.
37. Weiner, F. et al. (1995) *Cancer Res.* 55, 1181-8.

TABLE 1

| Cell type | Name | Species | Characteristics of cells |
|---|---|---|---|
| lymphocyte | SPL (spleen) | Mouse, BALB/c | Primary, diploid |
| PreB lymphocyte | Pre-B | Mouse, BALB/c | Cell line, near diploid |
| Pro B lymphocyte | BAF3 | Mouse, BALB/c | Cell line, near tetraploid |
| Plasmacytoma | DCPC21 | Mouse, BALB/c | Primary tumor, near tetraploid |
| Plasmacytoma | v-abl/myc 1 | Mouse, BALB/c | Primary tumor, trisomy 11 |
| Plasmacytoma | v-abl/myc 2 | Mouse, BALB/c | Primary tumor, diploid |
| Lymphocyte | Hu Ly | Human | Primary, diploid |
| Fibroblast | GL85/89W | Human | Primary, diploid |
| Fibroblast | VH | Human | Primary, diploid |
| Keratinocyte | HaCaT | Human | Cell line, near tetraploid |
| Colon carcinoma | Colo320HSR | Human | Tumor cell line, aneuploid |
| Neuroblastoma | SH-EP | Human | Tumor cell line, aneuploid |
| Epithelial tissue | CRTL/HNSCC (control tissue) | Human | Primary epithelial tissue, control for HNSCC |
| Head and neck squamous cell carcinoma tissue | HNSCC | Human | Primary tumor tissue |
| Cervical biopsies (tissues) | Cervical biopsies | Human | Primary tissue |
| Breast cancer tissue | | Human | Primary tissue |
| Burkitt Lymphoma | Raji | Human | Tumor cell line |

Cells analyzed in this study. Summary of the primary, immortalized and Tumor cells, their designation, cell type and species origin. References to Culture conditions are given in Methods. Stimulation of primary mouse *qj and Human lymphocytes was performed with lipopolysaccharide* (LPS) (100 *mg/ml*) A*nd with phytohemagglutinin* (PHA) (10 *mg/ml*) *respectively. 5 mm frozen Sections of primary human epithelial and head and neck squamous cell Carcinoma tissues were done using M*icrom HM 560.

TABLE 2

| AREA | # CELLS ANALYSED | TOTAL # OF TELOMERE AGGREGATES | TOTAL # OF TRANSLOCATIONS | HISTOLOGY |
|---|---|---|---|---|
| FOCUS 1919 (14 DAYS) | | | | |
| 1 | 85 | 12 | 0 | Diffuse Plasma Cell Hyperplasia |
| 2 | 95 | 19 | 0 | Plasma Cell Aggregates (Milky Spots) |
| 3 | 62 | 7 | 2 | Plasma Cell Aggregates (Milky Spots) |
| 4 | 119 | 18 | 4 | Plasma Cell Aggregates (Milky Spots) |
| 5 | 168 | 14 | 11 | Plasma Cell Aggregates (Milky Spots) |
| | TOTAL: 529 | TOTAL: 70 | TOTAL: 17 | |
| FOCUS 1937 (19 DAYS) | | | | |
| 1 | Autofluorescence - Not Analyzed | | | |
| 2 | 123 | 1 | 2 | Typical Plasma Cell Focus |
| 3 | 219 | 16 | 3 | Aggregates of Small Lymphocytes Associated with Plasma Cell Accumulations |
| 4 | 247 | 26 | 0 | Aggregates of Small Lymphocytes Associated with Plasma Cell Accumulations |
| 5 | 112 | 25 | 0 | Aggregates of Small Lymphocytes Associated with Plasma Cell Accumulations |
| | TOTAL: 701 | TOTAL: 68 | TOTAL: 5 | Aggregates of Small Lymphocytes Associated with Plasma Cell Accumulations |
| FOCUS 1938 (19 DAYS) | | | | |
| 1 | 31 | 0 | 25 | Plasmacytotic foci |
| 2 | | | | |
| 3 | 122 | 1 | 0 | Plasmacytotic foci |
| 4 | 165 | 0 | 0 | Plasmacytotic foci |
| 5 | 114 | 6 | 10 | Plasmacytotic foci |
| 6 | 39 | 2 | 13 | Plasmacytotic foci |
| | TOTAL: 471 | TOTAL: 9 | TOTAL: 48 | | p value of telomere aggregates: 0.8031
p value of dividing cells: 0.0077
p value of translocations: 0.0102

| | 1919 | 1937 | 1938 |
|---|---|---|---|
| Inter-Mice Differences in Telomere Aggregates | | | |
| 1919 | | 0.5664 | 0.9799 |
| 1937 | 0.5664 | | 0.5806 |
| 1938 | 0.9799 | 0.5806 | |
| Inter-Mice Differences in Dividing Cells | | | |
| 1919 | | 0.0082 | 0.7857 |
| 1937 | 0.0082 | | 0.007 |
| 1938 | 0.7857 | 0.007 | |
| Inter-Mice Differences in Translocations | | | |
| 1919 | | 0.355 | 0.0083 |
| 1937 | 0.355 | | 0.0061 |
| 1938 | 0.0083 | 0.0061 | |

TABLE 3

| Patient# | Image # | # aggregates | # dividing telomeres | Disk |
|---|---|---|---|---|
| *Human Colon Cancer: telomeres* | | | | |
| Colo 320 HSR | 1 | 4 | 2 | Yes |
| | 2 | 5 | 1 | Yes |
| | 3 | 5 | 1 | No |
| | 4 | 3 | 1 | No |
| | 5 | 2 | 1 | Yes |
| | 6 | 1 | 1 | Yes |
| | 7 | 2 | 2 | Yes |
| | 8 | 3 | 0 | No |
| | 9 | 5 | 2 | No |
| | 10 | 3 | 1 | No |
| | 11 | 7 | 1 | Yes |
| | 12 | 8 | 1 | No |
| | 13 | 5 | 3 | Yes |
| | 14 | 5 | 2 | No |
| | 15 | 3 | 3 | No |
| | 16 | 2 | 1 | No |
| | 17 | 4 | 2 | Yes |
| | 18 | 4 | 0 | No |
| | 19 | 3 | 2 | Yes |
| | 20 | 4 | 2 | Yes |
| | 21 | 5 | 1 | Yes |
| | Total | Total # of aggregates | Total # of dividing telomeres | Disk |
| | 21 | 83 | 30 | 11 |
| | | 100% of cells have aggregates (21/21) | 90.48% of cells have dividing telomeres (19/21) | |

| Patient# | Image # | Mixed chromosome signature |
|---|---|---|
| *Human Colon Cancer: chromosome Colo cell with Chr1:Chr2* | | |
| Colo 320 HSR | 1 | No |
| | 2 | Yes |
| | 3 | Yes |
| | 4 | Yes |
| | 5 | Yes |
| | 6 | Yes |
| | 7 | No |
| | 8 | Yes |
| | 9 | Yes |
| | 10 | Yes |
| | 11 | Yes |
| | 12 | Yes |
| | 13 | Yes |
| | 14 | Yes |
| | 15 | Yes |

TABLE 4

| image# | # aggregate (s) | # dividing telomere (s) | Disk |
|---|---|---|---|
| *Shep-cyto-telo* | | | |
| 1 | 2 | 2 | No |
| 2 | 1 | 0 | Yes |
| 3 | 3 | 1 | Yes |
| 4 | 4 | 1 | No |
| 5 | 3 | 2 | No |
| 6 | 5 | 2 | Yes |
| 7 | 2 | 5 | Yes |
| 8 | 0 | 0 | No |
| 9 | 1 | 1 | Yes |
| 10 | 3 | 2 | Yes |
| 11 | 1 | 0 | Yes |
| 12 | 1 | 0 | No |
| 13 | 1 | 0 | Yes |
| 14 | 2 | 1 | Yes |
| 15 | 3 | 1 | Yes |
| 16 | 2 | 0 | No |
| 17 | 1 | 0 | Yes |
| 18 | 1 | 3 | No |
| 19 | 1 | 1 | No |
| 20 | 0 | 0 | No |
| Total | Total # of aggregates | Total # of dividing telomeres | Disk |
| 20 | 37 | 22 | 11 |
| | 90% of cells have aggregates (18/20) | 60% of cells have dividing telomeres (12/20) | |

TABLE 5

Diagnosis: HNSCC

| Image # | # cells/image | # cells with aggregate | # aggregates/cell | # aggregates/image | # dividing telomeres |
|---|---|---|---|---|---|
| 2 | 1 | 0 | No aggregate | 0 | 0 |
| 3 | 1 | 0 | No aggregate | 0 | 0 |
| 4 | 1 | 0 | No aggregate | 0 | 1 |
| 5 | 1 | 2 | 1 cell with 2 aggregates | 4 | 2 |
| 6 | 2 | 1 | 1 cell with 1 aggregate | 1 | 1 |
| 7 | 1 | 1 | 1 cell with 1 aggregate | 1 | 1 |
| 8 | 0 | 0 | No aggregate | 0 | 1 |
| 9 | 1 | 1 | 1 cell with 1 aggregate | 1 | 1 |
| 10 | 1 | 0 | No aggregate | 0 | 0 |
| 11 | 1 | 1 | 1 cell with 2 aggregates | 2 | 4 |
| 12 | 1 | 0 | No aggregate | 0 | 1 |
| 13 | 1 | 0 | No aggregate | 0 | 2 |
| 14 | 1 | 1 | 1 cell with 1 aggregate | 1 | 1 |
| 15 | 1 | 0 | No aggregate | 0 | 1 |
| 16 | 2 | 1 | 1 cell with 1 aggregate | 1 | 4 |
| 17 | 1 | 0 | No aggregate | 0 | 1 |
| 18 | 1 | 0 | No aggregate | 0 | 3 |
| 19 | 1 | 0 | No aggregate | 0 | 0 |
| 20 | 1 | 1 | 1 cell with 1 aggregate | 1 | 1 |
| 21 | 1 | 0 | No aggregate | 0 | 0 |
| 22 | 2 | 0 | No aggregate | 0 | 1 |
| 23 | 4 | 1 | 1 cell with 1 aggregate | 1 | 3 |
| 24 | 1 | 0 | No aggregate | 0 | 1 |

TABLE 5-continued

Diagnosis: HNSCC

| | | | | | |
|---|---|---|---|---|---|
| 25 | 1 | 1 | 1 cell with 1 aggregate | 1 | 1 |
| 26 | 2 | 1 | 1 cell with 1 aggregate | 1 | 2 |
| 27 | 1 | 1 | 1 cell with 1 aggregate | 1 | 1 |
| 28 | 1 | 1 | 1 cell with 1 aggregate | 1 | 0 |
| 29 | 1 | 0 | No aggregate | 0 | 1 |
| 31 | 1 | 1 | 1 cell with 2 aggregates | 2 | 0 |
| 1 | 1 | 0 | No aggregate | 0 | 2 |
| 2 | 1 | 1 | 1 cell with 4 aggregates | 4 | 1 |
| 3 | 2 | 1 | 1 cell with 1 aggregate | 1 | 1 |
| 5 | 1 | 0 | No aggregate | 0 | 5 |
| 7 | 1 | 1 | 1 cell with 1 aggregate | 1 | 1 |
| 9 | 2 | 1 | 1 cell with 1 aggregate | 1 | 2 |
| 10 | 2 | 1 | 1 cell with 1 aggregate | 1 | 1 |
| 11 | 1 | 0 | No aggregate | 0 | 6 |
| 12 | 1 | 0 | No aggregate | 0 | 2 |
| 13 | 1 | 1 | 1 cell with 1 aggregate | 1 | 3 |
| 14 | 1 | 1 | 1 cell with 1 aggregate | 1 | 5 |
| 15 | 1 | 0 | No aggregate | 0 | 2 |
| 16 | 1 | 2 | 1 cell with 2 aggregates | 4 | 2 |
| 17 | 1 | 0 | No aggregate | 0 | 2 |
| 18 | 1 | 0 | No aggregate | 0 | 0 |
| 19 | 1 | 0 | No aggregate | 0 | 0 |
| 20 | 1 | 1 | 1 cell with 1 aggregate | 1 | 0 |

| Total # of cells | Total # of cells with aggregate | Total # of aggregates | Total # of dividing telomeres |
|---|---|---|---|
| 55 | 25 | 18 cells with 1 aggregate | 70 |
| | | 6 cells with 2 aggregates | |
| | | 1 cell with 4 aggregates | |
| | 45.45% cells with aggregate | | |

TABLE 6

RAJI

| image# | # aggregates | # dividing telomeres | Disk |
|---|---|---|---|
| 1 | 1 giant aggregate | 3 | too few telomere No |
| 2 | 1 | 5 | No |
| 3 | 2 | 4 | No |
| 4 | 1 | 5 | No |
| 5 | 0 | 1 | No |
| 6 | 0 | 0 | No |
| 7 | 1 | 0 | No |
| 8 | 0 | 5 | No |
| 9 | 1 | 1 | No |
| 10 | 1 | 2 | No |
| 11 | 0 | 3 | No |
| 12 | 1 big aggregate | 0 | too few telomere No |
| 13 | 0 | 4 | No |
| 14 | 1 | 2 | No |
| 15 | 0 | 2 | No |
| 16 | 2 | 0 | No |
| 17 | 1 | 2 | No |
| 18 | 3 big aggregates | 0 | No |
| 19 | 2 | 3 | No |
| 20 | 2 | 7 | No |
| 21 | 0 | 8 | No |
| 22 | 1 | 1 | No |
| 23 | 1 | 2 | No |
| 24 | 0 | 4 | No |
| 25 | 3 | 1 | No |
| 26 | 7 | 3 | No |
| 27 | 2 | 3 | No |
| 28 | 1 | 4 | No |
| 29 | 0 | 3 | No |
| 30 | 2 | 2 | No |
| 31 | 1 | 8 | No |
| 32 | 1 | 1 | No |
| 33 | 1 | 1 | No |
| 34 | 2 | 2 | No |
| 35 | 1 | 3 | No |
| Total | Total # of aggregates | Total # of dividing telomeres | Disk |
| 35 | 43 | 95 | — |
| | 74.29% of cells have aggregates (26/35) | 85.71% of cells have dividing telomeres (30/35) | |

TABLE 7

Patient 2087-03 (Cervical Dysplasia Grading: CIN III, Carcinoma In Situ)

| Image# | #cells/ image | #cells with aggregate | #aggregate/cell | #aggregate/ image | #dividing telomere | Disk |
|---|---|---|---|---|---|---|
| 1 | 2 | 1 | 1 cell with 1 aggregate | 1 | 1 | No |
| 2 | 3 | 0 | no aggregate | 0 | 3 | No |

TABLE 7-continued

Patient 2087-03 (Cervical Dysplasia Grading: CIN III, Carcinoma In Situ)

| 3 | 1 | 1 | 1 cell with 1 aggregate | 1 | 3 | No |
|---|---|---|---|---|---|---|
| 4 | 1 | 0 | no aggregate | 0 | 2 | No |
| 5 | 7 | 0 | no aggregate | 0 | 4 | No |
| 6 | 3 | 0 | no aggregate | 0 | 3 | No |
| 7 | 4 | 1 | 1 cell with 1 aggregate | 1 | 4 | No |
| 8 | 1 | 1 | 1 cell with 2 aggregates | 2 | 2 | No |

| Total # of cells | Total # of cells with aggregate | Total # of aggregates | Total # of dividing telomeres | Total # of Disk |
|---|---|---|---|---|
| 22 | 4<br>13.79% cells with aggregate | 3 cells with 1 aggregate<br>1 cell with 2 aggregates | 22 | — |

TABLE 8

| | # of Cells Analyzed | # of Cells with TA | # of TA per Cell |
|---|---|---|---|
| Control | | | |
| Patient 1 | 33 | 0 | 0 |
| Patient 2 | 27 | 0 | 0 |
| Breast Cancer | | | |
| Patient 1 | 492 | 134 (27.2%) | 78 cells with 1 TA<br>33 cells with 2 TA<br>13 cells with 3 TA<br>7 cells with 4 TA<br>3 cells with 6 TA |
| Patient 2 | 257 | 72 (28.0%) | 57 cells with 1 TA<br>8 cells with 2 TA<br>4 cells with 3 TA<br>1 cell with 4 TA<br>2 cells with 5 TA |
| Patient 3 | 388 | 27 (6.7%) | 26 cells with 1 TA<br>1 cell with 2 TA |
| Patient 4 | 72 | 55 (76.4%) | 55 cells with 1 TA |
| Patient 5 | 398 | 132 (33.2%) | 129 cells with 1 TA<br>3 cells share 1 TA |
| Patient 6 | 62 | 49 (79.0%) | 2 × 2 cells share 1 TA<br>2 × 3 cells share 1 TA<br>2 × 4 cells share 1 TA<br>1 × 5 cells share 1 TA |

TABLE 10

| Chro11 telo-v-alb-myc PCT | | | |
|---|---|---|---|
| image# | # aggregate (s) | # dividing telomere (s) | Disk |
| 2 | 11 | 1 | Yes |
| 3 | 4 | 3 | Yes |
| 4 | 2 | 2 | Yes |
| 5 | 8 | 2 | Yes |
| 6 | 4 | 3 | Yes |
| 7 | 7 | 2 | Yes |
| 8 | 10 | 2 | No |
| 9 | 9 | 2 | Yes |
| 10 | 4 | 3 | Yes |
| 11 | 5 | 1 | No |
| 12 | 8 | 3 | Yes |
| 13 | 7 | 3 | Yes |
| 14 | 8 | 1 | Yes |
| 15 | 5 | 2 | Distorted disc |
| 16 | 5 | 2 | Distorted disc |
| 17 | 5 | 2 | Distorted disc |
| 18 | 4 | 3 | Yes |
| 19 | 6 | 1 | Yes |
| 20 | 5 | 1 | Yes |
| 21 | 5 | 2 | Yes |

TABLE 9

| | −4HT | | | +4HT | | | |
|---|---|---|---|---|---|---|---|
| Time | # of nuclei with telomeric aggregations | # of nuclei with single telomeric aggregations | # of nuclei with multiple telomeric aggregations | # of nuclei with telomeric aggregations | # of nuclei with single telomeric aggregations | # of nuclei with multiple telomeric aggregations | p value |
| 0 hour | 2/21 (9.5%) | 2 | 0 | 2/21 (9.5%) | 2 | 0 | 0.8839 |
| 24 hours | 2/20 (10%) | 2 | 0 | 6/23 (26.1%) | 4 | 2 | 0.1607 |
| 48 hours | 0/20 (0%) | 0 | 0 | 6/22 (28.5%) | 4 | 2 | 0.0129 |
| 72 hours | 0/14 (0%) | 0 | 0 | 8/14 (57.1) | 4 | 4 | 0.0012 |
| 6 days | 1/14 (7.1%) | 1 | 0 | 4/19 (21.1%) | 2 | 2 | 0.229 |
| 10 days | 0/20 (0%) | 0 | 0 | 1/21 (4.8%) | 1 | 0 | 0.407 |

TABLE 10-continued

| Chro11 telo-v-alb-myc PCT ||||
| --- | --- | --- | --- |
| image# | # aggregate (s) | # dividing telomere (s) | Disk |
| Total | Total # of aggregates | Total # of dividing telomeres | Disk |
| 20 | 122 | 41 | 18 |
| | 100% of cells have aggregates (20/20) | 100% of cells have dividing telomeres (20/20) | |

TABLE 11

| Chromosome | +4HT/−4HT | [t] | both |
| --- | --- | --- | --- |
| 1 | | | |
| 2 | | 0.015 | <0.001 |
| 3 | | | |
| 4 | | 0.015 | |
| 5 | 0.001 | | |
| 6 | | | |
| 7 | | 0.0063 | |
| 8 | | 0.0003 | |
| 9 | | | |
| 10 | 0.018 | | |
| 11 | | | |
| 12 | | | |
| 13 | 0.011 | 0.0118 | |
| 14 | | 0.0001 | 0.0094 |
| 15 | | 0.001 | |
| 16 | | | |
| 17 | | 0.0156 | |
| 18 | | 0.0284 | 0.0349 |
| 19 | | | |
| X | | | |
| Y | | | 0.014 |

We claim:

1. A method for characterizing a 3D organization of telomeres and/or chromosomes, the method comprising:
   (i) inputting image data of the 3D organization of telomeres and/or chromosomes;
   (ii) processing the image data using an image data processor to find a set of coordinates $\{(x_i,y_i,z_i)\}$, $i=1, \ldots, N$, where $(x_i,y_i,z_i)$ is a position of the ith telomere and/or chromosome;
   (iii) finding a plane that is closest to the set of coordinates; and
   (iv) finding a set of distances $\{d_i\}$, $i=1, \ldots, N$, where $d_i$ is the distance between $(x_i,y_i,z_i)$ and the plane, wherein the set $\{d_i\}$ is utilized to characterize the 3D organization.

2. The method according to claim 1, wherein the 3D organization is characterized by specifying at least one of $\bar{d}$ and $\sigma$, where $\bar{d}$ is the average distance of the set of distances, and $\sigma$ is the standard deviation of the set of distances.

3. The method according to claim 2, wherein said characterization is used to monitor and/or diagnose disease by comparing the at least one of $\bar{d}$ and $\sigma$ to a corresponding control value.

4. The method according to claim 3, wherein the disease is a cell proliferative disorder.

5. The method according to claim 4, wherein the disease is cancer.

6. A method of monitoring or detecting genomic instability in a test cell, wherein the telomeric and/or chromosomal organization is characterized according to claim 1, comparing the telomeric/chromosomal organization in the test cell with that of a control value, wherein a change in telomeric/chromosomal organization in the test cell compared to the control value indicates the presence of genomic instability.

7. A method of characterizing a 3D organization of telomeres and/or chromosomes, the method comprising
   (i) inputting image data of the 3D organization of telomeres and chromosomal structures; and
   (ii) using an image data processor for finding a three dimensional geometrical shape that best encompasses the 3D organization, wherein the geometrical shape is an ellipsoid having principal axes $\alpha_1$, $\alpha_2$, and $\alpha_3$ and wherein said shape is used to characterize the 3D organization.

8. The method according to claim 7, wherein the ellipsoid is an oblate spheroid with $a_1$ approximately equal to $\alpha_2$.

9. The method according to claim 8, wherein an oblateness ratio, $\alpha_3/\alpha_1$ or $\alpha_1/\alpha_3$, is used to characterize the 3D organization.

10. A method of monitoring or detecting genomic instability in a test cell, wherein the telomeric and/or chromosomal organization is characterized according to claim 7, comparing the telomeric/chromosomal organization in the test cell with that of a control value, wherein a change in telomeric/chromosomal organization in the test cell compared to the control value indicates the presence of genomic instability.

11. The method of claim 7, wherein the image data is of the 3D organization of human telomeres and chromosomal structures.

12. A method for characterizing a 3D organization of telomeres and or chromosomes, the method comprising
   (i) inputting image data of the 3D organization of telomeres and/or chromosomes; and
   (ii) obtaining from the image data using an image data processor at least one of a set of intensities $\{I_i\}$, a set of volumes $\{V_i\}$ and a set of three dimensions $\{(Dx_i,Dy_i,Dz_i)\}$, $i=1, \ldots, N$, where $I_i$ is a total or average intensity, $V_i$ is a volume, and $(Dx_i,Dy_i,Dz_i)$ are principle axes of an ellipsoid describing the ith telomere and/or chromosome, respectively, wherein the at least one is utilized to characterize the 3D organization.

13. The method according to claim 12, wherein said characterization is used to monitor and/or diagnose disease by comparing a quantity obtained from at least one to a control value.

14. The method according to claim 13, wherein the disease is a cell proliferative disorder.

15. The method according to claim 14, wherein the cell proliferative disorder is cancer.

16. The method according to claim 13, wherein the quantity is an average of the members of $\{I_i\}$, $\{V_i\}$ or $(Dx_i,Dy_i,Dz_i)$.

17. A method of monitoring or detecting genomic instability in a test cell, wherein the telomeric and/or chromosomal organization is characterized according to claim 12, comparing the telomeric/chromosomal organization in the test cell with that of a control value, wherein a change in telomeric/chromosomal organization in the test cell compared to the control value indicates the presence of genomic instability.

18. A system for characterizing a 3D organization of telomeres and/or chromosomes, the system comprising
   (i) an input module for inputting image data of the 3D organization of telomeres and/or chromosomes;
   (ii) an image data processor for processing the image data to find a set of coordinates $\{(x_i,y_i,z_i)\}$, $i=1, \ldots, N$, where $(x_i,y_i,z_i)$ is a position of the ith telomere and/or chromosome;
   (iii) an optimizer for finding a plane that is closest to the set of coordinates; and (iv) a characteristic module for finding a set of distances $\{d_i\}$, i=1, ..., N, where $d_i$ is the distance between $(x_i,y_i,z_i)$ and the plane, wherein the set $\{d_i\}$ is utilized to characterize the 3D organization.

19. The system according to claim 18, wherein the 3D organization is characterized by specifying at least one of $\bar{d}$ and $\sigma$, where $\bar{d}$ is the average distance of the set of distances, and $\sigma$ is the standard deviation of the set of distances.

20. The system according to claim 19, further comprising a diagnosis module for comparing the at least one of $\bar{d}$ and $\sigma$ to a corresponding standard value to monitor or diagnose disease.

21. The system according to claim 20, wherein the disease is a cell proliferative disorder.

22. The system according to claim 21, wherein the cell proliferative disorder is cancer.

23. The system of claim 18, wherein the image data processor is coupled to a storage medium.

24. The system of claim 18 further comprising a microscope for obtaining image data.

25. The system of claim 18 further comprising a display unit for visually displaying the 3D organization of the telomeres and/or the chromosomes.

26. A system for characterizing a 3D organization of telomeres and/or chromosomes, the system comprising
(i) an input module for inputting image data of the 3D organization of telomeres and/or chromosomes;
(ii) an image data processor for processing the image data to find a set of coordinates $\{(x_i,y_i,z_i)\}$, i=1, ..., N, where $(x_i,y_i,z_i)$ is a position of the ith telomere and/or chromosome;
(iii) a characteristic module for finding a three dimensional geometrical shape that best encompasses the 3D organization, wherein the geometrical shape is an ellipsoid having principal axes $\alpha_1$, $\alpha_2$, and $\alpha_3$ and wherein said shape is used to characterize the 3D organization.

27. The system according to claim 26, wherein the ellipsoid is an oblate spheroid with $\alpha_1$ approximately equal to $\alpha_2$.

28. The system according to claim 27, wherein the ratio $\alpha_1/\alpha_3$ or $\alpha_3/\alpha_1$ is used to characterize the 3D organization.

29. The system of claim 26, wherein the image data processor is coupled to a storage medium.

30. The system of claim 26 further comprising a microscope for obtaining image data.

31. The system of claim 26 further comprising a display unit for visually displaying the 3D organization of the telomeres and/or the chromosomes.

32. The method of claim 26, wherein the image data is of the 3D organization of human telomeres and chromosomal structures.

33. A system for characterizing a 3D organization of telomeres and/or chromosomes, the system comprising
(i) an input module for inputting image data of the 3D organization of telomeres;
(ii) an image data processor for processing the image data to find a set of coordinates $\{(x_i,y_i,z_i)\}$, i=1, ..., N, where $(x_i,y_i,z_i)$ is a position of the ith telomere and/or chromosome; and
(iii) a characteristic module for obtaining from the image data at least one of a set of intensities $\{I_i\}$, a set of volumes $\{V_i\}$ and a set of three dimensions $\{(Dx_i,Dy_i,Dz_i)\}$, i=1, ..., N, where $I_i$ is a total or an average intensity, $V_i$ is a volume, and $(Dx_i,Dy_i,Dz_i)$ are principle axes of an ellipsoid describing the ith telomere, respectively, wherein the at least one is utilized to characterize the 3D organization.

34. The system according to claim 33, further comprising a diagnosis module for diagnosing disease by comparing a quantity obtained from the at least one to a standard value.

35. The system according to claim 34, wherein the disease is a cell proliferative disorder.

36. The system according to claim 35, wherein the cell proliferative disorder is cancer.

37. The system according to claim 34, wherein the quantity is an average of the members of $\{I_i\}$, $\{V_i\}$ or $(Dx_i,Dy_i,Dz_i)$.

38. The system of claim 33, wherein the image data processor is coupled to a storage medium.

39. The system of claim 33 further comprising a microscope for obtaining image data.

40. The system of claim 33 further comprising a display unit for visually displaying the 3D organization of the telomeres and/or the chromosomes.

41. A method for characterizing a 3D organization of telomeres and/or chromosomes, the method comprising
(i) inputting image data of the 3D organization of telomeres and/or chromosomes; and
(ii) using an image data processor for finding a parameter of the 3D organization that measures a deviation of the 3D organization from a planar arrangement, the deviation used to characterize the 3D organization.

42. A method of monitoring or detecting genomic instability in a test cell, wherein the telomeric and/or chromosomal organization is characterized according to claim 41, comparing the telomeric/chromosomal organization in the test cell with that of a control value, wherein a change in telomeric/chromosomal organization in the test cell compared to the control value indicates the presence of genomic instability.

43. A system for characterizing a 3D organization of telomeres and/or chromosomes, the system comprising
(i) an input module for inputting image data of the 3D organization of telomeres and/or chromosomes;
(ii) an image data processor for processing the image data to find a set of coordinates $\{(x_i,y_i,z_i)\}$, i=1, ..., N, where $(x_i,y_i,z_i)$ is a position of the ith telomere and/or chromosome; and
(iii) a characteristic module for finding a parameter of the distribution that measures a deviation of the distribution from a planar arrangement, the deviation used to characterize the 3D organization.

44. The system of claim 43, wherein the image data processor is coupled to a storage medium.

45. The system of claim 43 further comprising a microscope for obtaining image data.

46. The system of claim 43 further comprising a display unit for visually displaying the 3D organization of the telomeres and/or the chromosomes.

47. A method for characterizing a 3D organization of telomeres and/or chromosomes, the method comprising:
(i) obtaining image data of the 3D organization of telomeres and/or chromosomes using a microscope;
(ii) inputting the image data of the 3D organization of telomeres and/or chromosomes obtained using the microscope;
(iii) processing the image data to find a set of coordinates $\{(x_i,y_i,z_i)\}$, i=1, ..., N, where $(x_i,y_i,z_i)$ is a position of the ith telomere and/or chromosome;
(iv) finding a plane that is closest to the set of coordinates; and
(v) finding a set of distances $\{d_i\}$, i=1, ..., N, where $d_i$ is the distance between $(x_i,y_i,z_i)$ and the plane, wherein the set $\{d_i\}$ is utilized to characterize the 3D organization.

48. A method of characterizing a 3D organization of telomeres and/or chromosomes, the method comprising:

obtaining image data of the 3D organization of telomeres and/or chromosomes using a microscope;
(ii) inputting the image data of the 3D organization of telomeres and chromosomal structures obtained using the microscope; and
(iii) finding a three dimensional geometrical shape that best encompasses the 3D organization, wherein the geometrical shape is an ellipsoid having principal axes $\alpha_1, \alpha_2$, and $\alpha_3$ and wherein said shape is used to characterize the 3D organization.

49. A method for characterizing a 3D organization of telomeres and or chromosomes, the method comprising:
obtaining image data of the 3D organization of telomeres and/or chromosomes using a microscope;
(ii) inputting the image data of the 3D organization of telomeres and/or chromosomes obtained using the microscope; and
(iii) obtaining from the image data at least one of a set of intensities $\{I_i\}$, a set of volumes $\{V_i\}$ and a set of three dimensions $\{(Dx_i, Dy_i, Dz_i)\}$, i=1, ..., N, where $I_i$ is a total or average intensity, $V_i$ is a volume, and $(Dx_i, Dy_i, Dz_i)$ are principle axes of an ellipsoid describing the ith telomere and/or chromosome, respectively, wherein the at least one is utilized to characterize the 3D organization.

50. A method for characterizing a 3D organization of telomeres and/or chromosomes, the method comprising:
obtaining image data of the 3D organization of telomeres and/or chromosomes using a microscope;
(ii) inputting the image data of the 3D organization of telomeres and/or chromosomes obtained using the microscope; and
(iii) finding a parameter of the 3D organization that measures a deviation of the 3D organization from a planar arrangement, the deviation used to characterize the 3D organization.

51. A method for characterizing a 3D organization of telomeres and/or chromosomes, the method comprising:
obtaining image data of the 3D organization of telomeres and/or chromosomes using a microscope;
(ii) inputting the image data of the 3D organization of telomeres and/or chromosomes;
(iii) processing the image data to find a set of coordinates $\{(x_i, y_i, z_i)\}$, i=1, ..., N, where $(x_i, y_i, z_i)$ is a position of the ith telomere and/or chromosome;
(iv) finding a plane that is closest to the set of coordinates;
(v) finding a set of distances $\{d_i\}$, i=1, ..., N, where $d_i$ is the distance between $(x_i, y_i, z_i)$ and the plane, wherein the set $\{d_i\}$ is utilized to characterize the 3D organization.
(vi) visually displaying the 3D organization of the telomeres and/or chromosomes.

52. A method of characterizing a 3D organization of telomeres and/or chromosomes, the method comprising
obtaining image data of the 3D organization of telomeres and/or chromosomes using a microscope;
(ii) inputting the image data of the 3D organization of telomeres and chromosomal structures;
(iii) finding a three dimensional geometrical shape that best encompasses the 3D organization, wherein the geometrical shape is an ellipsoid having principal axes $\alpha_1, \alpha_2$, and $\alpha_3$ and wherein said shape is used to characterize the 3D organization; and
(iv) visually displaying the 3D organization of the telomeres and/or chromosomes.

53. A method for characterizing a 3D organization of telomeres and or chromosomes, the method comprising
obtaining image data of the 3D organization of telomeres and/or chromosomes using a microscope;
(ii) inputting the image data of the 3D organization of telomeres and/or chromosomes;
(iii) obtaining from the image data at least one of a set of intensities $\{I_i\}$, a set of volumes $\{V_i\}$ and a set of three dimensions $\{(Dx_i, Dy_i, Dz_i)\}$, i=1, ..., N, where $I_i$ is a total or average intensity, $V_i$ is a volume, and $(Dx_i, Dy_i, Dz_i)$ are principle axes of an ellipsoid describing the ith telomere and/or chromosome, respectively, wherein the at least one is utilized to characterize the 3D organization; and
(iv) visually displaying the 3D organization of the telomeres and/or chromosomes.

54. A method for characterizing a 3D organization of telomeres and/or chromosomes, the method comprising:
obtaining image data of the 3D organization of telomeres and/or chromosomes using a microscope;
(ii) inputting the image data of the 3D organization of telomeres and/or chromosomes; and
(iii) finding a parameter of the 3D organization that measures a deviation of the 3D organization from a planar arrangement, the deviation used to characterize the 3D organization; and
(iv) visually displaying the 3D organization of the telomeres and/or chromosomes.

\* \* \* \* \*

UNITED STATES PATENT AND TRADEMARK OFFICE
CERTIFICATE OF CORRECTION

PATENT NO. : 7,801,682 B2
APPLICATION NO. : 10/546152
DATED : September 21, 2010
INVENTOR(S) : Sabine Mai et al.

It is certified that error appears in the above-identified patent and that said Letters Patent is hereby corrected as shown below:

In Col. 34, Line 14, replace is an oblate spheroid with $a_1$ approximately equal to "2' with -- oblate spheroid with $a_1$ approximately equal to $a_2$." --;

In Col. 35, Line 31, should read -- (xi,yi,zi) is a position of the ith telomere and/or chromosome; "and" --;

In Col. 36, Line 63, replace (v) finding a set of distances {di}, i=1,...,N, where 'di' is with -- (v) finding a set of distances $\{d_i\}$, $i=1,...,N$, where $d_i$ is --;

In Col. 37, Line 1 and 2, replace 'obtaining image data of the 3D organization of telomeres and/or chromosomes using a microscope'; with -- "(i)" obtaining image data of the 3D organization of telomeres and/or chromosomes using a microscope --;

In Col. 37, Line 13, replace 'obtaining image data of the 3D organization of telomeres and/or chromosomes using a microscope'; with -- "(i)" obtaining image data of the 3D organization of telomeres and/or chromosomes using a microscope --;

In Col. 37, Line 28, replace 'obtaining image data of the 3D organization of telomeres and/or chromosomes using a microscope'; with -- "(i)" obtaining image data of the 3D organization of telomeres and/or chromosomes using a microscope --;

In Col. 37, Line 40, replace 'obtaining image data of the 3D organization of telomeres and/or chromosomes using a microscope'; with -- "(i)" obtaining image data of the 3D organization of telomeres and/or chromosomes using a microscope --;

In Col. 38, Line 3, replace "set {di} is utilized to characterize the 3D organization.' with -- set {di} is utilized to characterize the 3D organization; "and" --;

In Col. 38, Line 8, replace 'obtaining image data of the 3D organization of telomeres and/or chromosomes using a microscope'; with -- "(i)" obtaining image data of the 3D organization of telomeres and/or chromosomes using a microscope --;

Signed and Sealed this

Twenty-third Day of November, 2010

David J. Kappos
*Director of the United States Patent and Trademark Office*

CERTIFICATE OF CORRECTION (continued)
U.S. Pat. No. 7,801,682 B2

In Col. 38, Line 21, replace 'obtaining image data of the 3D organization of telomeres and/or chromosomes using a microscope'; with -- "(i)" obtaining image data of the 3D organization of telomeres and/or chromosomes using a microscope --;

In Col. 38, Line 37, replace 'obtaining image data of the 3D organization of telomeres and/or chromosomes using a microscope'; with -- "(i)" obtaining image data of the 3D organization of telomeres and/or chromosomes using a microscope --;

UNITED STATES PATENT AND TRADEMARK OFFICE
CERTIFICATE OF CORRECTION

PATENT NO. : 7,801,682 B2
APPLICATION NO. : 10/546152
DATED : September 21, 2010
INVENTOR(S) : Sabine Mai et al.

It is certified that error appears in the above-identified patent and that said Letters Patent is hereby corrected as shown below:

On the title page item (75), the list of named inventors should read: Sabine Mai, Tony Chih Yuan Chuang, Sharareh Moshir, Yuval Garini and Bartholomeus J. Vermolen.

Signed and Sealed this
Eighth Day of March, 2016

Michelle K. Lee
*Director of the United States Patent and Trademark Office*